United States Patent [19]
Ife

[11] Patent Number: 5,250,527
[45] Date of Patent: Oct. 5, 1993

[54] PYRIDYL CONTAINING BENZIMIDAZOLES, COMPOSITIONS AND USE

[75] Inventor: Robert J. Ife, Stevenage, England

[73] Assignee: SmithKline & French Laboratories Limited, Welwyn Garden City, England

[21] Appl. No.: 249,209

[22] Filed: Sep. 23, 1988

Related U.S. Application Data

[63] Continuation-in-part of Ser. No. 92,251, Sep. 2, 1987, abandoned, which is a continuation-in-part of Ser. No. 44,880, Apr. 30, 1987, abandoned, which is a continuation-in-part of Ser. No. 790,994, Oct. 24, 1985, abandoned.

[51] Int. Cl.$^5$ .................. A61K 31/44; A61K 31/535; C07D 401/12; C07D 413/14
[52] U.S. Cl. .................. 514/234.5; 514/253; 514/318; 514/338; 544/124; 544/131; 544/364; 546/193; 546/271
[58] Field of Search .................. 544/124, 131, 364; 546/193, 271; 514/234.5, 253, 318, 338

[56] References Cited

U.S. PATENT DOCUMENTS

| | | | |
|---|---|---|---|
| 4,045,564 | 8/1977 | Berntsson et al. | 546/271 |
| 4,359,465 | 11/1982 | Ruwart | 514/338 |
| 4,619,997 | 10/1986 | Sih | 544/124 |
| 5,075,323 | 12/1991 | Fain et al. | 514/338 |

*Primary Examiner*—Robert W. Ramsuer
*Attorney, Agent, or Firm*—Dara L. Dinner; Stephen Venetianer; Edward T. Lentz

[57] ABSTRACT

The invention relates to 4-amino-2-pyridylmethylsulfinyl-(and thio)-benzimidazoles which are inhibitors of potassium stimulated $H^+$-$K^+$ ATPase activity. A compound of the invention is 2-(4-amino-5-bromo-2-pyridylmethylsulphinyl)-5-methoxy-(1H)-benzimidazole.

25 Claims, No Drawings

PYRIDYL CONTAINING BENZIMIDAZOLES, COMPOSITIONS AND USE

This is a continuation of U.S. Ser. No. 092,251 filed Sep. 2, 1987 now abandoned, which is a continuation-in-part of U.S. Ser. No. 044,880 filed Apr. 30, 1987 now abandoned, which is a continuation-in-part of U.S. Ser. No. 790,994 filed Oct. 24, 1985 now abandoned.

The present invention relates to novel substituted benzimidazole derivatives, intermediates useful in their preparation, pharmaceutical compositions containing them and a method of inhibiting gastric acid secretion by administering them.

Substituted benzimidazole derivatives that are capable of inhibiting gastric acid secretion are known in the art. For example, U.S. Pat. No. 4,045,564 and U.S. Pat. No. 4,045,563 disclose a series of 2-pyridylalkylthio- and 2-pyridylalkylsulphinyl benzimidazoles in which the pyridyl group is optionally mono-substituted by an alkyl or a halogen group. Further, U.S. Pat. No. 4,255,431, U.S. Pat. No. 4,472,409 and EP 74341A disclose series of 2-pyridylalkylsulphinyl- and 2-pyridylalkylthiobenzimidazoles in which the pyridyl group is optionally substituted by 1 to 3 substituents selected from methyl, ethyl, methoxy, ethoxy, methoxyethoxy or ethoxyethoxy; and GB 2134523A discloses further such compounds in which the pyridyl group is optionally substituted by 1 to 3 groups. Such compounds are believed to exert their effects by inhibition of the gastrointestinal $H^+-K^+$ ATPase enzyme (Fellenius E., Berglindh T., Sachs G., Olke L., Elander B., Sjostrand, S. E. and Wallmark B. 1981, *Nature*, 290, 159–61).

In addition, U.S. Pat. No. 4359465 discloses the cytoprotective action of certain 2-pyridylalkylthio- and 2-pyridylalkylsulphinyl benzimidazoles and their use in the treatment or prevention of gastrointestinal inflammatory disease.

The compounds of the present invention are 2-pyridylalkylsulphinyl- and 2-pyridylalkylthio-benzimidazoles in which the 2-pyridyl group is substituted in the 4-position by an optionally substituted amino group, and are inhibitors of potassium stimulated $H^+-K^+$ ATPase activity.

The present invention therefore provides, in a first aspect, a compound of structure (I)

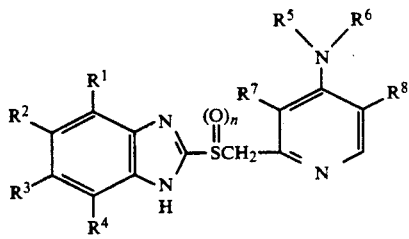

in which,
$R^1$ to $R^4$ are the same or different and are each hydrogen, halogen, trifluoromethyl, $C_{1-6}$alkyl, $C_{1-6}$alkoxy, $C_{1-6}$alkanoyl, $C_{1-6}$alkoxycarbonyl, $RCF_2O$, an ethoxy group substituted by 3 to 5 fluorine atoms, or $R^2$ and $R^3$ together form a group —$O(CR_2)_mO$—;
R is hydrogen or fluorine;
m is 1 or 2;
n is 0 or 1;
$R^5$ and $R^6$ are the same or different and are each hydrogen, $C_{1-6}$alkyl or $C_{3-6}$cycloalkyl or $R^5$ and $R^6$ together with the nitrogen atom to which they are attached form an azetidino, pyrrolidino, piperidino, piperazino, N—$C_{1-4}$alkylpiperazino or morpholino group; and
one of $R^7$ and $R^8$ is halogen, and the other is hydrogen, halogen or $C_{1-6}$alkyl;
or a pharmaceutically acceptable salt thereof.

Suitably, $R^1$ to $R^4$ are all hydrogen. Preferably $R^1$ and $R^4$ are hydrogen, one of $R^2$ and $R^3$ is hydrogen and the other is halogen, trifluoromethyl, $C_{1-6}$alkyl, $C_{1-6}$alkoxycarbonyl or $C_{1-6}$alkanoyl. More preferably, $R^1$ and $R^4$ are hydrogen, one of $R^2$ and $R^3$ is hydrogen and the other is $C_{1-6}$alkoxy, $RCF_2O$ or an ethoxy group substituted by 3 to 5 fluorine atoms; or, $R^1$ and $R^4$ are hydrogen and $R^2$ and $R^3$ together form a group —$O(CR_2)_mO$—.

Suitably, ethoxy groups substituted by 3 to 5 fluorine atoms are, 2,2,2-trifluoroethoxy, 1,1,2-trifluoroethoxy, 1,2,2-trifluoroethoxy, 1,2,2,2-tetrafluoroethoxy and perfluoroethoxy. Preferably, ethoxy groups substituted by 3 to 5 fluorine atoms are 1,1,2,2-tetrafluoroethoxy.

Suitably, groups —$O(CR_2)_mO$— in which m is 1 are methylenedioxy (—$OCH_2O$—); preferably difluoromethylenedioxy (—$OCF_2O$—). Suitably, groups —$O(CR_2)_mO$— in which m is 2 are ethylenedioxy (—$OCH_2CH_2O$—); preferably, trifluoroethylenedioxy (—$OCHFCF_2O$—).

Suitably n is 0. Preferably n is 1.

Suitably one of $R^5$ and $R^6$ is hydrogen and the other is $C_{3-6}$cycloalkyl. Preferably $R^5$ and $R^6$ are the same or different and are each hydrogen or $C_{1-6}$alkyl.

Suitably $R^5$ and $R^6$ together with the nitrogen to which they are attached form an azetidino group. Preferably, $R^5$ and $R^6$ together with the nitrogen to which they are attached form a morpholino, pyrrolidono, piperazino, N—$C_{1-4}$ alkylpiperazino or a piperidino group.

Suitably $R^7$ and $R^8$ are both halogen.
Preferably, one of $R^7$ and $R^8$ is halogen and the other is hydrogen or $C_{1-6}$alkyl.

$C_{1-6}$Alkyl groups alone or as part of another group (for example $C_{1-6}$alkoxy, $C_{1-6}$alkoxycarbonyl or $C_{1-6}$alkanoyl), can be straight or branched, for example methyl, ethyl, n-propyl, i-propyl, i-butyl, s-butyl, n-butyl, n-pentyl, i-pentyl or n-hexyl. Preferably $C_{1-6}$alkyl groups are methyl or ethyl.

Preferably, $C_{1-6}$alkoxy groups are methoxy or ethoxy.

Preferably $C_{1-6}$alkoxycarbonyl groups are methoxycarbonyl or ethoxycarbonyl.

Preferably $C_{1-6}$alkanoyl groups are methanoyl or ethanoyl.

$C_{3-6}$Cycloalkyl groups are cyclopropyl, cyclobutyl, cyclopentyl and cyclohexyl. Preferably, $C_{3-6}$cycloalkyl groups are cyclopentyl or cyclohexyl.

Halogen groups are fluorine, chlorine, bromine or iodine. Preferably halogen groups are fluorine, chlorine or bromine.

Preferred compounds of the present invention include
(i) compounds of structure (I) in which $R^5$ and $R^6$ are both $C_{1-6}$alkyl, for example,
2-(5-chloro-4-dimethylamino-2-pyridylmethylsulphinyl)-5-methoxy-(1H)-benzimidazole 2-(3-chloro-4-dimethylamino-2-pyridylmethylsulphinyl)-5-methoxy-(1H)-benzimidazole
2-(3-methyl-5-chloro-4-dimethylamino-2-pyridylmethylsulphinyl)-5-methoxy-(1H)-benzimidazole
2-(3-chloro-5-methyl-4-dimethylamino-2-pyridylmethylsulphinyl)-5-methoxy-(1H)-benzimidazole
2-(5-bromo-4-dimethylamino-2-pyridylmethylsulphinyl)-5methoxy-(1H)-benzimidazole
2-(4-dimethylamino-5-fluoro-2-pyridylmethylsulphinyl)-5-methoxy-(1H)-benzimidazole
2-(4-dimethylamino-3-fluoro-2-pyridylmethylsulphinyl)-5-methoxy-(1H)-benzimidazole
2-(4-dimethylamino-3-fluoro-2-pyridylmethylsulphinyl)-4,5-dimethoxy-(1H)-benzimidazole (ii) compounds of structure (I) in which $R^5$ and $R^6$ together form a morpholino, pyrollidino, piperazino, N—$C_{1-4}$alkylpiperazino or piperidino group, for example, 2-(3-chloro-4-morpholino-2-pyridylmethylsulphinyl)-5-methoxy-(1H)-benzimidazole
2-(3-chloro-5-methyl-4-morpholino-2-pyridylmethylsulphinyl)-5-methoxy-(1H)-benzimidazole
2-(5-chloro-4-piperidino-2-pyridylmethylsulphinyl)-5-methoxy-(1H)-benzimidazole
2-(3-chloro-4-piperidino-2-pyridylmethylsulphinyl)-5-methoxy-(1H)-benzimidazole
2-(3-methyl-5-chloro-4-piperidino-2-pyridylmethylsulphinyl)-5-methoxy-(1H)-benzimidazole
2-(3-chloro-5-methyl-4-piperidino-2-pyridylmethylsulphinyl)-5-methoxy-(1H)-benzimidazole
2-(5-chloro-4-pyrrolidino-2-pyridylmethylsulphinyl)-5-methoxy-(1H)-benzimidazole
2-(3-chloro-4-pyrrolidino-2-pyridylmethylsulphinyl)-5-methoxy-(1H)-benzimidazole
2-(3-methyl-5-chloro-4-pyrrolidino-2-pyridylmethylsulphinyl)-5-methoxy-(1H)-benzimidazole
2-(3-chloro-5-methyl-4-pyrrolidino-2-pyridylmethylsulphinyl)-5-methoxy-(1H)-benzimidazole
2-(5-bromo-4-pyrrolidino-2-pyridylmethylsulphinyl)-5-methoxy-(1H)-benzimidazole
2-(3-bromo-4-piperidino-2-pyridylmethylsulphinyl)-5-methoxy-(1H)-benzimidazole
2-(3-methyl-5-bromo-4-piperidino-2-pyridylmethylsulphinyl)-5-methoxy-(1H)-benzimidazole
2-(5-bromo-4-piperidino-2-pyridylmethylsulphinyl)-5-methoxy-(1H)-benzimidazole.
2-(4-morpholino-3-fluoro-2-pyridylmethylsulphinyl)-5-methoxy-(1H)-benzimidazole
2-(4-morpholino-3-fluoro-2-pyridylmethylsulphinyl)-4,5-dimethoxy-(1H)-benzimidazole
2-(4-morpholino-5-fluoro-2-pyridylmethylsulphinyl)-5-methoxy-(1H)-benzimidazole
2-(4-morpholino-3-methyl-5-fluoro-2-pyridylmethylsulphinyl)-5-methoxy-(1H)-benzimidazole
2-(4-morpholino-3-fluoro-2-pyridylmethylsulphinyl)-5-methyl-6-methoxy-(1H)-benzimidazole (iii) compounds of structure (I) in which the substituent on the benzimidazole ring is a 1,1,2,2-tetrafluoroethoxy group or a difluoromethylenedioxy group, for example 2-(3-chloro-5-methyl-4-piperidino-2-pyridylmethylsulphinyl)-5-(1,1,2,2-tetrafluoroethoxy)-(1H)-benzimidazole
2-(3-chloro-5-methyl-4-piperidino-2-pyridylmethylsulphinyl)-4,5-difluoromethylenedioxy-(1H)-benzimidazole
2-(3-chloro-4-piperidino-2-pyridylmethylsulphinyl)-5-(1,1,2,2-tetrafluoroethoxy)-(1H)-benzimidazole
2-(3-chloro-4-piperidino-2-pyridylmethylsulphinyl)-4,5-difluoromethylenedioxy-(1H)-benzimidazole
2-(3-chloro-5-methyl-4-pyrollidino-2-pyridylmethylsulphinyl)-5-(1,1,2,2-tetrafluoroethoxy)-(1H)-benzimidazole
2-(3-chloro-5-methyl-4-pyrollidino-2-pyridylmethylsulphinyl)-4,5-difluoromethylenedioxy-(1H)-benzimidazole
2-(3-chloro-5-methyl-4-dimethylamino-2-pyridylmethylsulphinyl)-5-(1,1,2,2-tetrafluoroethoxy)-(1H)-benzimidazole, and
2-(3-chloro-5-methyl-4-dimethylamino-2-pyridylmethylsulphinyl)-4,5-difluoromethylenedioxy-(1H)-benzimidazole
2-(3-methyl-5-bromo-4-piperidino-2-pyridylmethylsulphinyl)-5-(1,1,2,2-tetrafluoroethoxy)-(1H)-benzimidazole
2-(3-methyl-5-bromo-4-piperidino-2-pyridylmethylsulphinyl)-4,5-difluoromethylenedioxy-(1H)-benzimidazole
2-(3-bromo-4-piperidino-2-pyridylmethylsulphinyl)-5-(1,1,2,2-tetrafluoroethoxy)-(1H)-benzimidazole
2-(5-bromo-4-piperidino-2-pyridylmethylsulphinyl)-5-(1,1,2,2-tetrafluoroethoxy)-(1H)-benzimidazole
2-(3-bromo-4-piperidino-2-pyridylmethylsulphinyl)-4,5-difluoromethylenedioxy-(1H)-benzimidazole
2-(5-bromo-4-piperidino-2-pyridylmethylsulphinyl)-4,5-difluoromethylenedioxy-(1H)-benzimidazole and (iv) the corresponding thioethers of the foregoing preferred compounds i.e. the analogous compounds of structure (I) in which n is 0.

Compounds of structure (I) in which n is 0, can form pharmaceutically acceptable acid addition salts with suitable organic and inorganic acids, the nature of which will be apparent to persons skilled in the art. For example, pharmaceutically acceptable salts can be formed by reaction with hydrochloric, sulphuric, sulphonic or phosphonic acids; aliphatic, alicyclic, aromatic or heterocyclic carboxyl or sulphonic acids; methionine, tryptophan, lysine or arginine and the like.

Compounds of structure (I) in which n is 1 can also form pharmaceutically acceptable acid addition salts, but in aqueous solution the salts are less stable than those formed with the compounds of structure (I) in which n is 0.

Compounds of structure (I) in which n is 1 can form basic salts by reaction with an appropriate base. Such salts include, for example, the sodium, potassium, lithium, calcium and magnesium salts which can be prepared by methods well known to those skilled in the art for example, the sodium, potassium and lithium salts can be prepared by reaction with sodium, potassium or lithium hydroxide in an aqueous or non-aqueous medium; and the calcium salts can be prepared by reaction with calcium chloride in an aqueous or non-aqueous medium.

Compounds of structure (I) in which n is 0 can also form basic salts but such salts are less stable than those prepared from compounds of structure (I) in which n is 1.

Compounds of structure (I) in which n is 1 have an asymmetric centre at the S atom and are thus optically active compounds. As such, these compounds exist as two optical isomers (enantismers). In addition, compounds of structure (I) in which one or more of $R^1$ to $R^8$ is a branched $C_{3-6}$alkyl group (either alone or as part of another group) may contain an additional asymmetric centre(s) due to the presence of the $C_{3-6}$alkyl group(s).

Again, such compounds will exist as two (or more) optical isomers.

Both the pure enantiomers, racemic mixtures (50% of each enantiomer) and unequal mixtures of the two are included within the scope of the present invention. Further, all diasteriomeric forms possible (pure enantiomers and mixtures thereof) are within the scope of the invention.

It should be noted that for all the compounds of the present invention, the substituents $R^1$ and $R^4$ as well as $R^2$ and $R^3$ are considered to be equivalent at room temperature in solution. This is due to the tautomerism of the benzimidazole nucleus causing an equilibrium between the 2 possible forms.

Processes for the preparation of compounds of structure (I) or pharmaceutically acceptable salts thereof comprise (a) reacting a compound of structure (II)

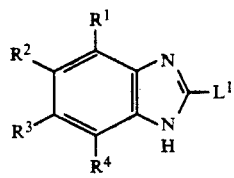

with a compound of structure (III)

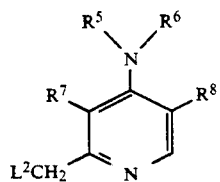

in which $R^1$ to $R^8$ are as described for structure (I) and one of $L^1$ and $L^2$ is SH and the other a leaving group displaceable by a mercaptan;

(b) reacting a compound of structure (IV)

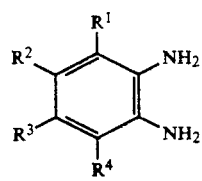

in which $R^1$ to $R^4$ are as described for structure (I), with a compound of structure (V)

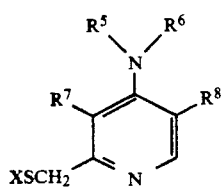

in which $R^5$ to $R^8$ are as described for structure (I), X is $CO_2H$ or $CSX^1$ and $X^1$ is halogen or $C_{1-4}$alkoxy;

(c) reacting a compound of structure (VI)

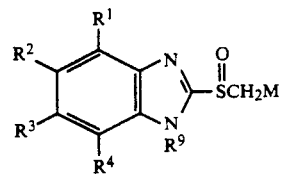

in which $R^1$ to $R^4$ are as described for structure (I), $R^9$ is hydrogen or a protecting group and M is an alkali metal atom, with a compound of structure (VII)

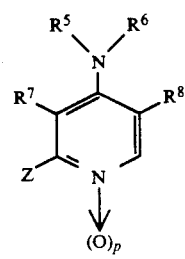

in which $R^5$ to $R^8$ are as described for structure (I), Z is a leaving group and p is 0 or 1;

(d) reacting a compound of structure (VIII)

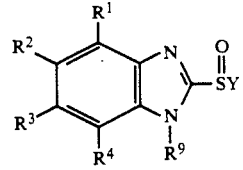

in which $R^1$ to $R^4$ are as described for structure (I), $R^9$ is hydrogen or a protecting group and Y is a leaving group, with a compound of structure (IX)

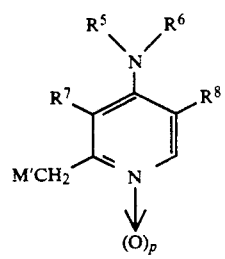

in which $R^5$ to $R^8$ are as described for structure (I), p is 0 or 1 and M' is an alkali metal atom or the equivalent of an alkali metal atom, and, optionally, where desired:

(i) oxidising a compound of structure (I) so formed in which n is 0 to a compound of structure (I) in which n is 1;

(ii) reducing a compound of structure (I) so formed in which n is 1 to a compound of structure (I) in which n is 0;

(iii) forming a pharmaceutically acceptable salt.

Suitable leaving groups $L^1$ displaceable by mercaptan include halogen, for example chloro, bromo or iodo, aryl sulphonyloxy for example toluenesulphonyloxy, alkylsulphonyloxy for example methanesulphonyloxy, alkylmercapto, for example methylmercapto, or alkylsulphinyl, for example methylsulphinyl.

Suitable leaving groups $L^2$ are as described for $L^1$, and may also be $C_{1-4}$acyloxy, for example acetoxy, or hydroxy.

Suitable alkali metal atoms include, for example lithium, sodium or potassium.

Suitable leaving groups Z include, for example, halogen (preferably chloro) and hydroxy activated by esterification with, for example, an aryl or alkane sulphonic acid. Suitable sulphonic acids will be apparent to those skilled in the art, for example p-toluenesulphonic acid or methanesulphonic acid.

Suitable leaving groups Y are those groups which form a reactive sulphinic acid derivative together with the sulphinyl group to which it is attached, and include for example, $C_{1-4}$ alkoxy, di-$C_{1-4}$ alkylamino and $C_{1-4}$ alkylmercapto.

Suitable groups M' which are equivalent to a metal atom include, for example, alkali earth metal atoms, (for example magnesium) which are substituted by a halogen atom (for example, bromine).

Suitable protecting groups $R^9$ are those conventional in the art for example as described in "Protective Groups in Organic Synthesis" T. W. Greene 1981 (Wiley). It will be appreciated that the group $R^9$ should not be cleavable under the conditions of reaction of compounds of structure (VIII) and (IX). Such groups include for example benzyl or trityl groups.

The reaction between compounds of structure (II) in which $L^1$ is SH and compounds of structure (III) in which $L^2$ is a leaving group can be carried out under basic conditions in the presence of an inert solvent at a temperature between ambient and the reflux temperature of the solvent.

Suitable solvents include lower alkanols, for example methanol or ethanol, mixtures of lower alkanols with water, or ethers for example dimethoxyethane or tehrahydrofuran.

Suitable bases will be apparent to those skilled in the art and include for example, alkali metal hydroxides, for example, sodium or potassium hydroxide, alkali metal alkoxides, for example potassium t-butoxide, alkali metal hydrides, for example sodium or potassium hydride, or organic tertiary amines, for example triethylamine.

Preferably the reaction is carried out at ambient temperature in ethanol as solvent, in the presence of sodium hydroxide solution.

It is to be noted, and will be apparent to persons skilled in the art that under basic conditions $L^2$ should be a group other than hydroxy or acetoxy, for example halogen, preferably chlorine.

Further, the reaction can be carried out under neutral conditions in the presence of an inert solvent at the reflux temperature of the solvent. Suitable solvents include those hereinbefore described.

Alternatively, when $L^2$ is hydroxy or $C_{1-4}$acyloxy, for example acetoxy, the reaction can be carried out under acidic conditions. Suitable acidic conditions will be well known to those skilled in the art, for example, under reflux in hydrobromic acid, optionally in the presence of acetic acid.

The reaction between compounds of structure (II) in which $L^1$ is a leaving group and compounds of structure (III) in which $L^2$ is SH can be carried out under basic conditions as described for the reaction between compounds of structure (II) in which $L^1$ is SH and compounds of structure (III) in which $L^2$ is a leaving group.

The reaction between compounds of structure (IV) and compounds of structure (V) can be carried out under acidic conditions in a suitable solvent at a temperature between ambient and reflux temperature of the solvent used.

Suitably the reaction is carried out in polar solvents, for example, lower alkanols, dimethyl sulphoxide, acetone, dimethylformamide or acetonitrile, optionally in the presence of water. Preferably the reaction is carried out in ethanol.

Suitably the reaction is carried out in the presence of a strong acid, for example hydrobromic or hydrochloric acid. Preferably the reaction is carried out in the presence of hydrochloric acid.

Preferably the reaction is carried out at the reflux temperature of the solvent.

The reaction between a compound of structure (VI) and a compound of structure (VII) can be carried out in an inert solvent at ambient or elevated temperature depending on the nature of groups M and Z. Suitable solvents include those solvents usually employed for the reaction of enolate ions with alkylating agents for example, benzene or toluene. Preferably, when M is lithium and Z is chlorine, the reaction is conducted in benzene at reflux temperature.

The reaction between a compound of structure (VIII) and a compound of structure (IX) can be carried out under conditions normally used for organometallic reactions as will be well known to those skilled in the art.

The products of reactions (a) to (c) are compounds of structure (I) in which n is 0. These products can be oxidised to compounds of structure (I) in which n is 1 by reaction with an oxidising agent. Suitable oxidising agents include, for example, nitric acid, hydrogen peroxide, peracids, peresters, ozone, dinitrogen tetroxide, iodosobenzene, N-halosuccinamide, 1-chlorobenzotriazole, hypohalites, for example sodium hypochlorite or t-butyl hypochlorite, diazabicylo [2,2,2]-octane bromine complex, sodium metaperiodate, selenium dioxide, manganese dioxide, chromic acid, ceric ammonium nitrate, bromine, chlorine, or sulphuryl chloride. Preferably the oxidising agent is m-chloroperbenzoic acid.

The oxidation reaction is carried out under conditions known in the art for the oxidation of thiols to sulphoxides. Suitably, the reaction is carried out in an inert solvent at a temperature of between $-70°$ and the boiling point of the solvent used. Suitable solvents include aromatic or chlorinated hydrocarbons, for example benzene, toluene, dichloromethane or chloroform, esters, for example ethyl acetate, or ethers, for example dioxan. Preferably, the reaction is carried out in dichloromethane at a temperature of between $-50°$ and $+20°$ C.

The compounds of structure (I) are obtained either as the free base, or in the form of a salt depending on the choice of starting materials and reaction conditions. If the free compound is obtained it can be converted into a salt by standard techniques well-known to those skilled in the art, for example by dissolving the compound in a suitable solvent and adding the desired acid or base; alternatively, if a salt is obtained it can be converted into the free compound, again by standard techniques, for example by treatment with an appropriate acid or base.

Racemic mixtures may be produced and can be separated by standard techniques e.g. recrystallisation from optically active solvent or by high performance liquid affinity chromatography as described by S. Allenmark, B. Bomgren, H. Baren and P-O Lagerstrom in Analytical Biochemistry, 136, 293-7, 1984.

The intermediate of structure (IV) and the intermediate benzimidazole structures (II), (VI) and (VIII) are known and can be prepared by methods analogous to those known in the art. For example, compounds of structure (II) in which $L^1$ is SH can be prepared by reacting the corresponding compounds of structure (IV) with carbon disulphide in the presence if alkali metal hydroxides, or with potassium ethylxanthate (Org. Syn., 30, 56 ) or thiophosgene. Compounds of structure (II) in which $L^1$ is a leaving group, for example halogen can be obtained from the corresponding compounds of structure (II) in which $L^1$ is hydroxy by treatment with for example, phosphorous oxychloride. The compounds of structure (II) in which $L^1$ is hydroxy can be prepared by reacting compounds of structure (IV) with phosgene. Compounds of structure (IV) can be prepared by methods analogous to those described in EP 127763 A, DE 2848531, CA, 60, 13352 h, 1964 and Liebigs Ann.Chem., 730, 16-30, 1969.

Compounds of structure (VI) can be prepared by methylation, oxidation and subsequent deprotection of compounds of structure (II) in which $L^1$ is SH using, for example, alkali metal hydroxides or alcoholates.

The intermediates of structures (III), (V), (VII) and (IX) are novel and provide a further aspect of the invention. They can be prepared by methods analogous to those well known in the art as described in "The Chemistry of Heterocyclic Compounds - Pyridine and its Derivatives", Pts. 2 and 3, E. Klingsberg Ed., Interscience Publishers, 1962. For example, (i) compounds of structure (III) in which $L^2$ is hydroxy and $R^5$ and $R^6$ are not both hydrogen can be prepared by the reactions outlined in Scheme 1.

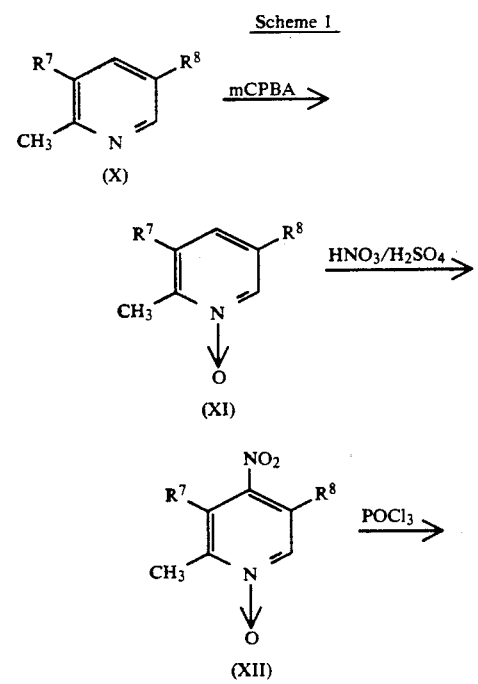

In Scheme 1, the 3 - or 5 -halo compounds of structure (X) are commercially available or can be prepared by standard methods as described in the examples herein.

(ii) compounds of structure (III) in which $L^2$ is hydroxy, $R^5$ and $R^6$ are not both hydrogen, one of $R^7$ and $R^8$ is bromine and the other is hydrogen or $C_{1-6}$alkyl can also be prepared by the methods outlined in Scheme 2.

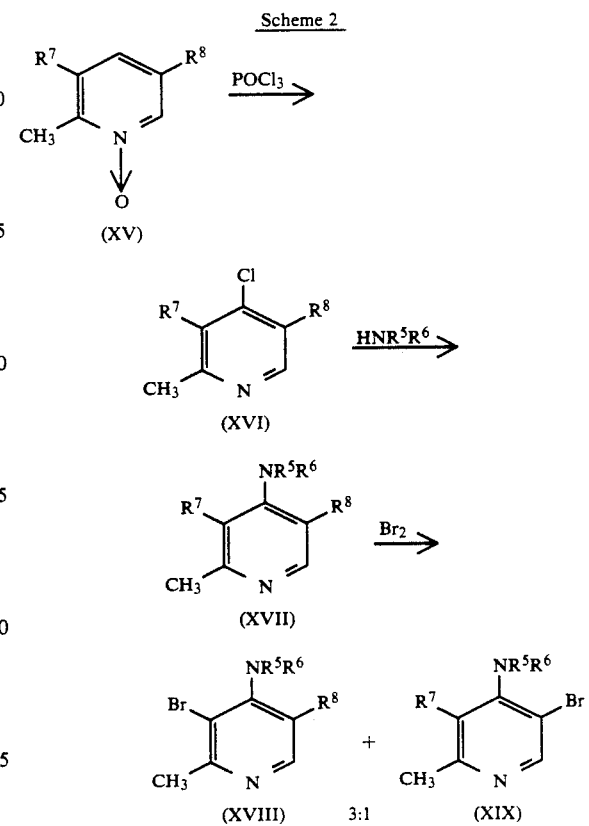

-continued
Scheme 2

$R^7 = R^8$ = hydrogen

Separation of the 3- and 5-bromo intermediates (XVIII) and (XIX) followed by oxidation to the corresponding N-oxides and rearrangement using, for example, acetic anhydride gives the required compounds of structure (III) in which one of $R^7$ and $R^8$ is bromine and the other is hydrogen. If, in the starting material of structure (XV) one of $R^7$ and $R^8$ is $C_{1-6}$alkyl and the other is hydrogen, then the bromination reaction gives essentially a single product, namely the 3-bromo-5-alkyl compounds (XVIII, $R^8 = C_{1-6}$ alkyl) or 3-alkyl-5-bromo compounds (XIX, $R^7 = C_{1-6}$alkyl). These products can be oxidised and rearranged as hereinbefore described to the desired compounds of structure (III) in which one of $R^7$ and $R^8$ is bromine and the other is $C_{1-6}$alkyl.

(iii) compounds of structure (III) in which $L^2$ is hydroxy, $R^5$ and $R^6$ are not both hydrogen, $R^7$ is chlorine and $R^8$ is hydrogen or $C_{1-6}$alkyl can be prepared by the reactions outlined in Scheme 3.

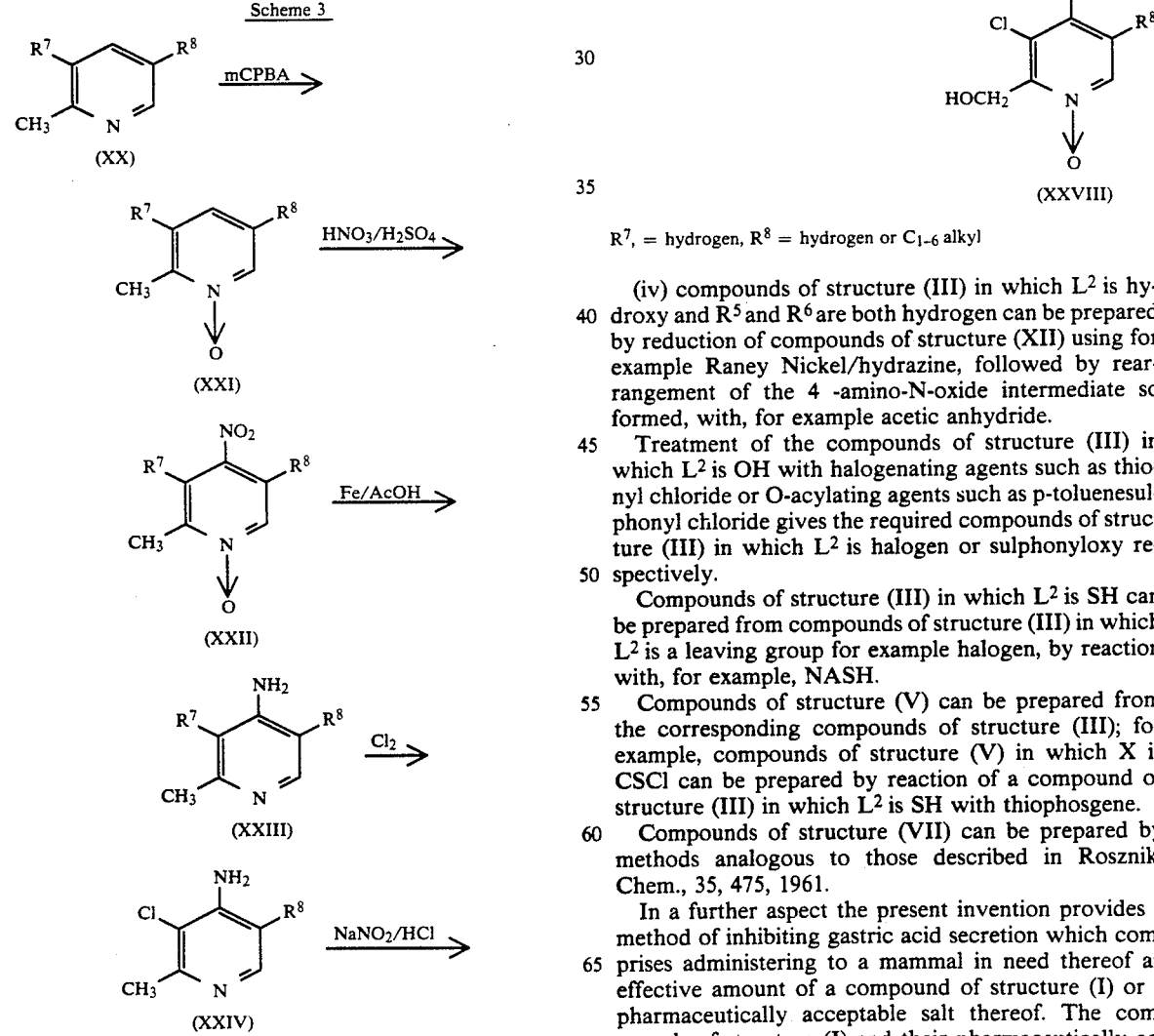

$R^7$ = hydrogen, $R^8$ = hydrogen or $C_{1-6}$ alkyl (iv) compounds of structure (III) in which $L^2$ is hydroxy and $R^5$ and $R^6$ are both hydrogen can be prepared by reduction of compounds of structure (XII) using for example Raney Nickel/hydrazine, followed by rearrangement of the 4-amino-N-oxide intermediate so formed, with, for example acetic anhydride.

Treatment of the compounds of structure (III) in which $L^2$ is OH with halogenating agents such as thionyl chloride or O-acylating agents such as p-toluenesulphonyl chloride gives the required compounds of structure (III) in which $L^2$ is halogen or sulphonyloxy respectively.

Compounds of structure (III) in which $L^2$ is SH can be prepared from compounds of structure (III) in which $L^2$ is a leaving group for example halogen, by reaction with, for example, NASH.

Compounds of structure (V) can be prepared from the corresponding compounds of structure (III); for example, compounds of structure (V) in which X is CSCl can be prepared by reaction of a compound of structure (III) in which $L^2$ is SH with thiophosgene.

Compounds of structure (VII) can be prepared by methods analogous to those described in Roszniki Chem., 35, 475, 1961.

In a further aspect the present invention provides a method of inhibiting gastric acid secretion which comprises administering to a mammal in need thereof an effective amount of a compound of structure (I) or a pharmaceutically acceptable salt thereof. The compounds of structure (I) and their pharmaceutically acceptable salts inhibit exogenously and endogenously stimulated gastric acid secretion and are useful in the treatment of gastrointestinal diseases and other conditions caused or exacerbated by gastric acidity in mammals, in particular humans. Such diseases include, for example, gastric and duodenal ulcers, and Zollinger-Ellison Syndrome.

Further, the compounds of structure (I) can be used in the treatment of other disorders where a cytoprotective and/or anti-secretory effect is desirable, for example, in patients with gastritis, NSAID induced gastritis, gastritis associated with a history of chronic and excessive alcohol consumption, gastric ulcers, acute upper gastrointestinal bleeding, for the prophylaxis of upper gastrointestinal haemmorage in patients at risk of the development of stress-related lesions of the gastric mucosa, and in the reduction of risk factors, for example gastric acidity and volume associated with pulmonary aspiration.

It is believed that, after administration to mammals, compounds of structure (I) in which n is 0 exert their anti-secretory and cytoprotective activities after conversion into compounds of structure (I) in which n is 1.

Furthermore it is believed that compounds of structure (I) in which n is 1, after administration to mammals, exert their anti-secretory activity after transformation under acid conditions into another chemically reactive species. Active species so generated from compounds of structure (I) are within the scope of the present invention.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compounds of structure (I) in which n is 1 are susceptible to decomposition in acid media, and thus tablets and capsules containing such compounds are preferably provided with an enteric coating to protect the compound from acid degradation in the stomach or capsules used which are inherently acid resistant. Alternatively, the enteric coating can be provided by coating pellets containing the active ingredient before filling them into the hard gelatin capsule. Suitable enteric coating materials are those well known in the art of pharmacy and include for example shellac or anionic-film forming polymers such as cellulose acetate phthalate and hydroxypropylmethyl cellulose phthalate and the like, optionally in the presence of a plasticizer.

It will be apparent to those skilled in the art that other standard techniques for enhancing the stability of such compounds can be used. The nature of such techniques will depend on the route of administration and include, for example, the formation of stable complexes with, for example $\beta$-cyclodextrin.

The compounds of structure (I) and their pharmaceutically acceptable salts which are active when administered parenterally (i.e. by injection or infusion) can be formulated as solutions or suspensions.

A composition for parenteral administration will generally consist of a solution or suspension of the active ingredient in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

A typical transdermal formulation comprises a conventional aqueous or non-aqueous vehicle, for example, a cream, ointment lotion or paste or in the form of a medicated plaster, patch or membrane.

A typical composition for inhalation comprises a solution, suspension or emulsion that may be administered in the form of an aerosol using a conventional propellant such as dichlorodifluoromethane or trichlorofluoromethane.

Preferably the composition is in unit dose form such as a tablet or capsule. Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The amount of compound of structure (I) or pharmaceutically acceptable salt thereof given to a patient will depend on the type and severity of the condition to be treated. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$- antagonists (for example, cimetidine).

The following examples illustrate the invention. Temperatures are recorded in degrees centigrade.

EXAMPLE 1 A

Preparation of 5 -bromo-2 -methyl-pyridine-N-oxide

To a solution of 5 -Bromo-2 -methyl-pyridine (71.35 g. 0.41 M) in dichloromethane (350 ml) was added a solution of m-chloroperbenzoic acid (78.83 g, 0.46 M) in dichloromethane (1100 ml), over a period of 2.5 hours. The reaction mixture was stirred at ambient temperature for a further 20 hours, cooled (ice/salt bath) and anhydrous ammonia bubbled into it for 1 hour during which time a white precipitate formed and the temperature of the solution was not allowed to rise above 151°. The reaction mixture was allowed to warm to room temperature, filtered and washed with dichloromethane. The filtrate and washings were combined and washed with $Na_2 SO_3$ (5 %) solution (2×200 ml), water (2×150 ml), dried (phase separating paper) and evaporated to dryness in vacuo to give an off white solid. Recrystallisation from ethyl acetate gave 5 -bromo-2 -methylpyridine-N-oxide as white crystals, 65.66 g. 84 %. m.p. 116°–118°.

EXAMPLE 1 B

Preparation of 5 -bromo-4 -nitro-2 -methylpyridine-N-oxide

The product of 1(A) (59.89 g. 0.32 M) was added in portions, over 45 minutes to a nitrating mixture consisting of conc. sulphuric acid (100 ml) and conc. nitric acid (100 ml). The reaction mixture was heated at 60 ° C. with stirring for 20 hours, allowed to cool and poured on to ice with stirring so that its temperature did not rise above 10°. Sodium hydroxide solution (10 N) was then added to give a final volume of 1700 ml at pH 12 (again, during addition of NAOH, the temperature not allowed to rise above 25 °).

The solution was then extracted with ethyl acetate (4×1000 ml), the extracts combined dried and evaporated in vacuo to give a suspension (400 ml). The suspension was heated, filtered and allowed to cool to give crystals (yellow needles) of the title compound 65.00 g, m.p. 137°–8°.

EXAMPLE 1 C

Preparation of 5 -Bromo-4 -amino-2 -methylpyridine-N-oxide

To a suspension of the product of example 1(B) (5.00 g, 0.02 M) in ethanol (100 ml) under an atmosphere of nitrogen was added Raney Nickel, followed by hydrazine hydrate (1.6 ml, 0.03 M) in ethanol (10 ml). The reaction mixture was stirred under nitrogen for 2.5 hours, a further portion of hydrazine hydrate (0.8 ml, 0.015 M) in ethanol (5 ml) added and the mixture stirred for a further 21 hours at ambient temperature. The mixture was filtered, washed through with ethanol, and the combined filtrates evaporated to dryness to give a brown oil. Column chromatography, using chloroform: methanol (30:1) as eluant gave the title compound 0.96 g. 25 %, m.p. 212°–215 ° (decomp).

EXAMPLE 1 D

Preparation of 5 -Bromo-4 -amino-2 -hydroxymethyl-pyridine

The product of example 1(C) (0.83 g. 0.0041 M) was heated under reflux in acetic anhydride (25 ml) for 2 hours. The mixture was evaporated to dryness, taken up in 2 N HCl (10 ml) and heated over a steam bath for 1 hour. The solution was cooled, extracted with chloroform and the aqueous layer basified to pH 11.5 with sodium hydroxide solution (ice bath) and extracted with ethyl acetate (5×50 ml). The combined extracts were evaporated to dryness to give, as an off-white glass, the title compound, 0.56 g.

EXAMPLE 1 E

Preparation of 5 -Bromo-4 -amino-2 -chloromethylpyridine hydrochloride

5 -Bromo-4 -amino-2 -hydroxymethylpyridine (0.60 g, 0.003 M) in chloroform (15 ml) was cooled to −10 ° and thionyl chloride (0.64 ml, 1.05 g, 0.0089 M) in chloroform (5 ml) added dropwise over 20 minutes so that the temperature of the reaction mixture did not rise above −10°. The reaction mixture was stirred for 1 hour at −10 ° and then allowed to warm to room temperature and stirred for 21 hours (if the reaction is not complete at this stage, further portions of thionyl chloride can be added (at −10 °), followed by reflux if necessary).

Excess thionyl chloride was destroyed by the dropwise addition of methanol and the mixture evaporated to dryness in vacuo to give the title compound as a brown glass, 0.76 g.

EXAMPLE 1 F

Preparation of 2 -(4 -amino-5 -bromo-2 -pyridylmethylthio)-5 -methoxy-(1H)-benzimidazole The product of example of 1 E (0.73 g, 0.0028 M) and 5 -methoxy-2 -mercapto-benzimidazole (0.51 g, 0.0028 M) were dissolved in ethanol (30 ml) and 5 N sodium hydroxide solution added (1.2 ml). The reaction mixture was stirred at room temperature for 22 hours and then evaporated to dryness in vacuo. The residue was dissolved in water (30 ml) and then basified with concentrated NAOH solution to pH 14. The solution was extracted with chloroform (3×100 ml), the organic layers dried, and then evaporated to dryness in vacuo, to give 2 -(4 -amino-5 -bromo-2 -pyridylmethylthio)-5 -methoxy-(1H)-benzimidazole 0.66 g, m.p. 183°–4°.

EXAMPLE 2

Preparation of 2 -(4 -amino-5 -bromo-2 -pyridyl-methylsulphinyl)-5 -methoxy-(1H)-benzimidazole 2 -(4 -amino-5 -bromo-2 -pyridylmethylthio)-5 -methoxy-(1H)-benzimidazole (0.58 g, 0.0016 M) was dissolved in dichloromethane (160 ml) and cooled to −40°. m-Chloroperbenzoic acid (0.33 g, 0.0019 M) in dichloromethane (10 ml) was added dropwise over 20 mins, keeping the temperature at 30 ° to −40°. The solution was stirred at −30 ° for 1 hour and then stored at −20 ° overnight, or until reaction was complete. Ammonia was then bubbled through the solution at 50, the mixture allowed to warm up to room temperature, and then filtered. The filtrate and washings were washed with 10 % $Na_2 CO_3$ (10 ml) an dried. Back extraction of the aqueous layers with dichloromethane (3×100 ml) gave further organic layers which were dried and combined with layers obtained from the first extraction. Evaporation of the combined organic layers gave a brown solid. Purification, by heating in presence of decolouring charcoal in ethyl acetate/methanol, followed by recrystallisation from methanol gave 2-(4-amino-5-bromo-2-pyridylmethylsulphinyl)-5-methoxy-(1H)-benzimidazole, 0.21 g, m.p. 130°-132°.

EXAMPLE 3 A

Preparation of 4-amino-3-chloro-2-picoline

Precondensed chlorine (ca. 20 ml) was evaporated into a stirred, ice cooled solution of 4-amino-2-picoline (44 g) in sulphuric acid (11, 50 % v/v) in a flask fitted with a dri-cold trap. After stirring for a further 2 hours the solution was basified (NAOH) and extracted with ether. The extract was dried ($K_2CO_3$), treated with charcoal and reduced to a small volume. Pet. ether (40/60) was added to give a solid which was recrystallised from chloroform/pet. ether (60/80) to give 4-amino-3-chloro-2-picoline, 37.2 g, m.p. 116°-18°.

EXAMPLE 3 B

Preparation of 3,4-dichloro-2-picoline

Sodium nitrite (36 g) was added in portions to a stirred solution of 4-amino-3-chloro-2-picoline (24.85 g) in conc. hydrochloric acid (750 ml) cooled to 0°-5°. After 1 hour at 0°-5° and a further 2 hours at room temperature the mixture was basified (NaOH), allowing the temperature to rise to ca. 50°, and extracted with ether. After drying ($K_2CO_3$), the extract was evaporated to dryness to give 3,4-dichloro-2-picoline (26.5 g) as a low melting solid.

EXAMPLE 3 C

Preparation of 3,4-dichloro-2-hydroxymethylpyridine m-Chloroperbenzoic acid (32.63 g) in dichloromethane (400 ml) was added dropwise to a solution of 3,4-dichloro-2-picoline (25.53 g)in dichloromethane (100 ml) maintaining the temperature at 20°-25°. After standing for 16 hours at room temperature the solution was washed with 1 N NAOH, dried ($K_2CO_3$) and filtered to give a pale yellow solution. Trifluoroacetic anhydride (30 ml) was added dropwise to this solution maintaining the temperature at 15°-20°. After standing for 2 days at room temperature, methanol (100 ml) was added and the solution evaporated under reduced presure. The residue was treated with aqueous sodium carbonate and extracted into dichloromethane. After drying ($K_2CO_3$) and removal of solvent, the residue was recrystallised from pet. ether (60/80) to give 3,4-dichloro-2-hydroxymethylpyridine, 15.76 g, m.p. 66°-8°.

EXAMPLE 3 D

Preparation of 4-morpholino-3-chloro-2-hydroxymethylpyridine

Morpholine (7.34 ml) and 3.4-dichloro-2-hydroxymethylpyridine (3.0 g) were heated together in a bomb at 180° for 4 hours. After cooling, the mixture was taken up in ethanol and evaporated under reduced pressure to remove excess amine. The residue was taken up in water and extracted with chloroform. After drying ($K_2CO_3$) and removal of solvent, the residue was chromatographed (silica gel, $CHCl_3$) to give an oil which was crystallised from petroleum ether (60/80) to give 4-morpholino-3-chloro-2-hydroxymethylpyridine, 3.24 g, m.p. 80°-2°.

EXAMPLE 3 E

Preparation of 4-morpholino-3-chloro-2-chloromethlpyridine hydrochloride

Thionyl chloride (3 ml) in chloroform (25 ml) was added dropwise to a solution of 4-morpholino-3-chloro-2-hydroxymethylpyridine (3.09 g) in chloroform (25 ml) cooled in an ice/salt bath. Following the addition the ice bath was removed and the mixture stirred for a further 1.5 hours. The volume of the solution was reduced and ether added to give 4-morpholino-3-chloro-2-chloromethylpyridine hydrochloride, 3.77 g, m.p. 200°-2°.

EXAMPLE 3 F

Preparation of 2-(4-morpholino-3-chloro-2-pyridylmethylthio)-5-methoxy-(1H)-benzimidazole 5 N Sodium hydroxide (5.68 ml) was added dropwise to a stirred solution of 4-morpholino-3-chloro-2-chloromethylpyridine hydrochloride (3.66 g) and 5-methoxy-2-mercaptobenzimidazole (2.33 g). After standing overnight the solution was evaporated under reduced pressure and the residue triturated with water. The solid thus obtained was recrystallised from ethanol to give 2-(4-morpholino-3-chloro-2-pyridyl-methyl-thio)-5-methoxy-(1H)-benzimidazole, 4.38 g, m.p. 124°-25°.

EXAMPLE 4

Preparation of 2-(4-morpholino-3-chloro-2-pyridylmethylsulphinyl)-5-methoxy-(1H)-benzimidazole A solution of m-chloroperbenzoic acid (1.61 g) in dichloromethane (75 ml) was added dropwise to a stirred solution of 2-(4-morpholino-3-chloro-2-pyridylmethylthio)-5-methoxy-(1H)-benzimidazole (3.35 g) in dichloromethane (150 ml) cooled to −35°. After 1 hour, ammonia was passed through the solution for 5 minutes and the precipitate filtered off. The solution was evaporated under reduced pressure and the residue chromatographed (silica gel, 2 % $CHCl_3$/MEOH-$NH_3$) to give an oil which was crystallised from ethanol to give 2-(4-morpholino-3-chloro-2-pyridylmethylsulphinyl)-5-methoxy-(1H)-benzimidazole. (2.6 g).

| 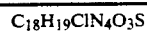 | |
|---|---|
| Found | C 53.39, H 4.79, N 13.62, S 7.75, Cl 8.84 |
| Requires | C 53.13, H 4.71, N 13.77, S 7.88, Cl 8.71 |

EXAMPLE 5 A

Preparation of 4-amino-3-chloro-2,5-dimethylpyridine

Substituting 4-amino-2.5-dimethylpyridine (35 g) for 4-amino-2-picoline and using corresponding molar proportions of the other reagents in the method of Example 3 A gave 4-amino-3-chloro-2,5-dimethylpyridine, 26 g, m.p. 82°-3°.

EXAMPLE 5 B

Preparation of 3,4-dichloro-2,5-dimethylpyridine

Substituting 4-amino-3-chloro-2,5-dimethylpyridine (26 g) for 4-amino-3-chloro-2-picoline and using corresponding molar proportions of the other reagents in the method of Example 3B gave 3,4-dichloro-2,5-dimethylpyridine, 26.8 g, as an oil.

EXAMPLE 5 C

Preparation of 3,4-dichloro-5-methyl-2-hydroxymethylpyridine

Substituting 3,4-dichloro-2,5-dimethylpyridine (26.8 g) for 3,4-dichloro-2-picoline and using corresponding molar proportions of the other reagents in the method of Example 3 C gave 3,4-dichloro-5-methyl-2-hydroxymethylpyridine, 22.5 g, m.p. 77°–8 ° from ether/pet. ether (40/60).

EXAMPLE 5 D

Preparation of 4-morpholino-3-chloro-5-methyl-2-hydroxymethylpyridine

Substituting 3,4-dichloro-5-methyl-2-hydroxymethylpyridine (4 g) for 3,4-dichloro-2-hydroxymethylpyridine and using corresponding molar proportions of the other reagents, in the method of Example 3 D gave 4-morpholino-3-chloro-5-methyl-2-hydroxymethylpyridine, 4.49 g, m.p. 54°–5 ° from pet. ether (60/80).

EXAMPLE 5 E

Preparation of 4-morpholino-3-chloro-5-methyl-2-chloromethylpyridine Hydrochloride Substituting 4-morpholino-3-chloro-5-methyl-2-hydroxymethylpyridine (4.0 g) for 4-morpholino-3-chloro-2-hydroxymethylpyridine and using corresponding molar proportions of the other reagents in the method of Example 3 E gave 4-morpholino-3-chloro-5-methyl-2-chloromethylpyridine hydrochloride, 4.9 g, m.p. 176°–90°.

EXAMPLE 5 F

Preparation of 2-(4-morpholino-3-chloro-5-methyl-2-pyridylmethylthio)-5-methoxy-(1H)-benzimidazole Substituting 4-morpholino-3-chloro-5-methyl-2-chloromethylpyridine hydrochloride (4.0 g) for 4-morpholino-3-chloro-2-chloromethylpyridine hydrochloride and using corresponding molar proportions of the other reagents in the method of Example 3 F gave 2-(4-morpholino-3-chloro-5-methyl-2-pyridylmethylthio)-5-methoxy-(1H)-benzimidazole, 3.96 g, m.p. 162°–4 ° from acetonitrile.

EXAMPLE 6

Preparation of 2-(4-morpholino-3-chloro-5-methyl-2-pyridylmethylsulphinyl)-5-methoxy-(1H)-benzimidazole Substituting 2-(4-morpholino-3-chloro-5-methyl-2-pyridylmethylthio)-5-methoxy-(1H)-benzimidazole (3.8 g) for 2-(4-morpholino-3-chloro-2-pyridylmethylthio)-5-methoxy-(1H)-benzimidazole and using corresponding molar proportions of the other reagents in the method of Example 4 gave, after chromatography (alumina CHCl$_3$/MEOH 0–1 %), 2-(4-morpholino-3-chloro-5-methyl-2-pyridylmethylsulphinyl)-5-methoxy-(1H)-benzimidazole, 1.09 g, m.p. 147°–48 ° from acetonitrile.

| | $C_{19}H_{21}ClN_4O_3S$ |
|---|---|
| Found | C 54.25, H 5.08, N 13.25. S 7.6, Cl 8.68 |
| Requires | C 54.22. H 5.03, N 13.31, S 7.62, Cl 8.42 |

EXAMPLE 7 A

Preparation of 4-piperidino-3-chloro-5-methyl-2-hydroxymethylpyridine

Substituting piperidine for morpholine in the method of Example 5 D, gave 4-piperidino-3-chloro-5-methyl-2-hydroxymethylpyridine (80 %) as an oil.

EXAMPLE 7 B

Preparation of 4-piperidino-3-chloro-5-methyl-2-chloromethylpyridine hydrochloride Substituting 4-piperidino-3-chloro-5-methyl-2-hydroxymethylpyridine (2.9 g) for 4-morpholino-3-chloro-5-methyl-2-hydroxymethylpyridine and using corresponding molar proportions of the other reagents in the method of Example 5 E gave 4-piperidino-3-chloro-5-methyl-2-chloromethylpyridine hydrochloride, 3.5 g, m.p. 178°–80°.

EXAMPLE 7 C

Preparation of 2-(4-piperidino-3-chloro-5-methyl-2-pyridylmethylthio)-5-methoxy-(1H)-benzimidazole Substituting 4-piperidino-3-chloro-5-methyl-2-chloromethylpyridine hydrochloride (3 g) for 4-morpholino-3-chloro-2-chloromethylpyridine hydrochloride and using corresponding molar proportions of the other reagents in the method of Example 5 F gave 2-(4-piperidino-3-chloro-5-methyl-2-pyridylmethylthio)-5-methoxy-(1H)-benzimidazole, 3.1 g, m.p. 154°–56 ° from acetonitrile.

EXAMPLE 8

Preparation of 2-(4-piperidino-3-chloro-5-methyl-2-pyridylmethylsulpinyl)-5-methoxy-(1H)-benzimidazole Substituting 2-(4-piperidino-3-chloro-5-methyl-2-pyridyl methylthio)-5-methoxy-(1H)-benzimidazole (2.3 g) for 2-(4-morpholino-3-chloro-5-methyl-2-pyridylmethylthio)-5-methoxy-(1H)-benzimidazole and using corresponding molar proportions of the other reagents, in the method of Example 6, gave 2-(4-piperidino-3-chloro-5-methyl-2-pyridylmethylsulphinyl)-5-methoxy-(1H)-benzimidazole, 0.78 g, m.p. 151°–52 ° from acetonitrile.

| | $C_{20}H_{23}ClN_4O_2S$ |
|---|---|
| Found | C 57.17, H 5.47, N 13.33, S 7.6, Cl 8.54 |
| Requires | C 57.34, H 5.55, N 13.37, S 7.65, Cl 8.46 |

EXAMPLE 9 A

Preparation of 4-piperidino-3-chloro-2-hydroxymethylpyridine

Substituting piperidine (7.17 g) for morpholine and using corresponding molar proportions of the other reagents, in the method of Example 3 D, gave 4-piperidino-3-chloro-2-hydroxymethyl pyridine, 2.7 g, m.p. 68°–70 ° from pet. ether (40/60).

EXAMPLE 9 B

Preparation of 4-piperidino-3-chloro-2-chloromethylpyridine hydrochloride

Substituting 4-piperidino-3-chloro-2-hydroxymethyl pyridine (3.43 g) for 4-morpholino-3-chloro-2

-hydroxymethyl pyridine and using corresponding molar proportions of the other reagents in the method of Example 3 E, gave 4 -piperidino-3 -chloro-2 -chloromethyl pyridine hydrochloride, 4.02 g, m.p. 192°–4°.

EXAMPLE 9 C

Preparation of 2 -(4 -piperidino-3 -chloro-2 -pyridylmethylthio)-5 -methoxy-(1H)-benzimidazole Substituting 4 -piperidino-3 -chloro-2 -chloromethylpyridine hydrochloride (3.87 g) for 4 -morpholino-3 -chloro-2 -chloromethyl pyridine hydrochloride and using corresponding molar proportions of the other reagents in the method of Example 3 F, gave 2 -(4 -piperidino-3 -chloro-2 -pyridylmethylthio)-5 -methoxy-(1H)-benzimidazole, 4.53 g, m.p. 145°–7°.

EXAMPLE 10

Preparation of 2 -(4 -piperidino-3 -chloro-2 -pyridylmethylsulphinyl)-5 -methoxy-(1H)-benzimidazole Substituting 2 -(4 -piperidino-3 -chloro-2 -pyridylmethylthio)-5-methoxy-(1H)-benzimidazole (4.12 g) for 2 -(4 -morpholino-3-chloro-2 -pyridylmethylthio)-5 -methoxy-(1H)-benzimidazole and using corresponding molar proportions of the other reagents, in the method of Example 4, gave 2 -(4 -piperidino-3-chloro-2 -pyridylmethylsulphinyl)-5 -methoxy-(1H)-benzimidazole, 1.51 g.

| | $C_{19}H_{21}ClN_4O_2S$ |
|---|---|
| Found | C 56.72, H 5.28, N 13.80, S 7.79, Cl 8.67 |
| Requires | C 56.36, H 5.23, N 13.81, S 7.92, Cl 8.76 |

EXAMPLE 11 A

Preparation of 4 -pyrrolidino-3 -chloro-2 -hydroxymethylpyridine

Substituting pyrrolidine (5.99 g) for morpholine and using corresponding molar proportions of the other reagents, in the method of Example 3 D, gave 4 -pyrrolidino-3 -chloro-2 -hydroxymethylpyridine, 3.0 g, m.p. 85°–6°.

EXAMPLE 11 B

Preparation of 4 -pyrrolidino-3 -chloro-2 -chloromethylpyridine hydrochloride

Substituting 4 -pyrrolidino-3 -chloro-2 -hydroxymethyl pyridine (2.96 g) for 4 -morpholino-3 -chloro-2 -hydroxymethylpyridine and using corresponding molar proportions of the other reagents, in the method of Example 3 E, gave 4-pyrrolidino-3 -chloro-2 -chloromethylpyridine hydrochloride, 3.68 g, m.p. 184°–5°.

EXAMPLE 11 C

Preparation of 2 -(4 -pyrrolidino-3 -chloro-2 -pyridylmethylthio)-5 -methoxy-(1H)-benzimidazole Substituting 4 -pyrrolidino-3 -chloro-2 -chloromethylpyridine hydrochloride (3.68 g) for 4 -morpholino-3 -chloro-2 -chloromethyl pyridine hydrochloride and using corresponding molar proportions of the other reagents in the method of Example 3 F gave 2 -(4 -pyrrolidino-3 -chloro-2 -pyridylmethylthio)-5 -(1H)-benzimidazole, 4.14 g, m.p. 131°–3°.

EXAMPLE 12

Preparation of 2 -(4 -pyrrolidino-3 -chloro-2 -pyridylmethylsulphinyl)-5 -methoxy-(1H)-benzimidazole Substituting 2 -(4 -pyrrolidino-3 -chloro-2 -pyridylmethylthio)-5 -methoxy-(1H)-benzimidazole (4.11 g) for 2 -(4 -morpholino-3 -chloro-2 -pyridylmethylthio)-5 -methoxy-(1H)-benzimidazole and using corresponding molar proportions of the other reagents in the method of Example 4 gave 2 -(4 -pyrrolidino-3 -chloro-2 -pyridylmethylsulphinyl)-5 -methoxy-(1H)-benzimidazole, 1.92 g.

| | $C_{18}H_{19}ClN_4O_2S$ |
|---|---|
| Found | C 54.98, H 4.90, N 14.15, S 8.28, C 19.25 |
| Requires | C 55.31, H 4.90, N 14.33, S 8.20, C 19.07 |

EXAMPLE 13 A

Preparation of 4 -pyrrolidino-3 -chloro-5 -methyl-2 -hydroxymethylpyridine

Substituting pyrrolidine for morpholine in the method of Example 5 D gave 4 -pyrrolidino-3 -chloro-5-methyl-2 -hydroxymethylpyridine (50 %) as an oil.

EXAMPLE 13 B

Preparation of 4 -pyrrolidino-3 -chloro-5 -methyl-2 -chloromethyl hydrochloride

Substituting 4 -pyrrolidino-3 -chloro-5 -methyl-2 -hydroxymethylpyridine (2.1 g) for 4 -morpholino-3 -chloro-5 -methyl-2 -hydroxymethylpyridine and using corresponding molar proportions of the other reagents in the method of Example 5 E gave 4 -pyrrolidino-3 -chloro-5 -methyl-2 -chloromethylpyridine hydrochloride, 2.38 g, m.p. 180°–182°.

EXAMPLE 13 C

Preparation of 2 -(4 -pyrrolidino-3 -chloro-5 -methyl-2 -pyridylmethylthio)-5 -methoxy-(1H)-benzimidazole Substituting 4 -pyrrolidino-3 -chloro-5 -methyl-2 -chloromethylpyridine hydrochloride (2.2 g) for 4 -morpholino-3 -chloro-5 -methyl-2 -chloromethylpyridine hydrochloride and using corresponding molar proportions of the other reagents in the method of Example 5 F gave 2 -(4 -pyrrolidino-3 -chloro-5 -methyl-2 -pyridylmethylthio)-5 -methoxy-(1H)-benzimidazole, 3.01 g, m.p. 152°–158 ° from acetonitrile.

EXAMPLE 14

Preparation of 2 -(4 -pyrrolidino-3 -chloro-5 -methyl-2 -pyridylmethylsulphinyl)-5 -methoxy-(1H)-benzimidazole Substituting 2 -(4 -pyrrolidino-3 -chloro-5 -methyl-2 -pyridylmethylthio)-5 -methoxy-(1H)-benzimidazole (2.3 g) for 2 -(4 -morpholino-3 -chloro-5 -methyl-2 -pyridylmethylthio)-5 -methoxy-(1H)-benzimidazole and using corresponding molar proportions of the other reagents in the method of Example 6 gave 2 -(4 -pyrrolidino-3 -chloro-5 -methyl-2 -pyridylmethylsulphinyl)-5 -methoxy-(1H)-benzimidazole, 1.74 g, m.p. 145°–146 ° from acetonitrile.

| | $C_{19}H_{21}ClN_4O_2S$ |
|---|---|
| Found | C 56.51, H 5.31, N 13.97, S 7.91, Cl 8.92 |
| Requires | C 56.36, H 5.23, N 13.84, S 7.92, Cl 8.76 |

EXAMPLE 15 A

Preparation of 4 -dimethylamino-3 -chloro-5 -methyl-2 -hydroxymethylpyridine 3,4 -dichloro-5 -methyl-2 -hydroxymethylpyridine (4 g) was dissolved in 33 % dimethylamine in ethanol (11 ml), placed in a sealed vessel and heated to 2000° C. for 4 hours. On cooling, the reaction mixture was evaporated under reduced presure and the residue dissolved in water (15 ml) and ether extracted. Etherial extracts were dried ($K_2CO_3$), filtered and stripped to yield 4 -dimethylamino-3 -chloro-5 -methyl-2 -hydroxymethylpyridine, 4.08 g as an oil.

EXAMPLE 15 B

Preparation of 4 -dimethylamino-3 -chloro-5 -methyl-2 -chloromethylpyridine hydrochloride Substituting 4 -dimethylamino-3 -chloro-5 -methyl-2 -hydroxymethylpyridine (3.5 g) for 4 -morpholino-3 -chloro-5 -methyl-2 -hydroxymethylpyridine and using corresponding molar proportions of the other reagents in the method of Example 5 E gave 4 -dimethylamino-3 -chloro-5 -methyl-2 -chloromethylpyridine hydrochloride, 4.0 g, m.p. 162°-163°.

EXAMPLE 15 C

Preparation of 2 -(4 -dimethylamino-3 -chloro-5 -methyl-2 -pyridylmethylthio)-5 -methoxy-(1H)-benzimidazole Substituting 4 -dimethylamino-3 -chloro-5 -methyl-2 -chloromethylpyridine hydrochloride (3.9 g) for 4 -morpholino-3 -chloro-5 -methyl-2 -pyridylmethylpyridine hydrochloride and using corresponding molar proportions of the other reagents in the method of Example 5 F gave 2 -(4 -dimethylamino-3 -chloro-5 -methyl-2 -pyridylmethylthio)-5 -methoxy-(1H)-benzimidazole, 4.2 g, m.p. 109°-110° from acetonitrile.

EXAMPLE 16

Preparation of 2 -(4 -dimethylamino-3 -chloro-5 -methyl-2 -pyridylmethylsulphinyl)-5 -methoxy-(1H)-benzimidazole Substituting 2 -(4 -dimethylamino-3 -chloro-5 -methyl-2 -pyridylmethylthio)-5 -methoxy-(1H)-benzimidazole (1.6 g) for 2 -(4 -morpholino-3 -chloro-5 -methyl-2 -pyridylmethylthio)-5 -methoxy-(1H)-benzimidazole and using corresponding molar proportions of the other reagents, in the method of Example 6, gave 2 -(4 -dimethylamino-3 -chloro-5 -methyl-2 -pyridylmethylsulphinyl)-5 -methoxy-(1H)-benzimidazole, 0.94 g, m.p. 147°-149 ° (from acetonitrile).

| | $C_{17}H_{19}ClN_4O_2S$ |
|---|---|
| Found | C 53.69, H 5.02, N 14.70, Cl 9.37, S 8.43 |
| Requires | C 53.89, H 5.05, N 14.79, Cl 9.36, S 8.46 |

EXAMPLE 17 A

Preparation of 4 -Piperidino-2 -picoline

Piperidine (31.7 ml) and 4 -chloro-2 -picoline (13.65 g) were heated together in a bomb at 170° for 4.5 hours. After cooling, the mixture was taken up in water and extracted with ether. After drying ($K_2CO_3$) and stripping, the residue was distilled to give 4 -piperidino-2 -picoline, 15.45 g, b.p. 105°-10 ° (0.1 mm).

EXAMPLE 17 B

Preparation of 4 -piperidino-5 -bromo-2 -picoline and 4 -piperidino-3 -bromo-2 -picoline A solution of bromine (9.3 ml) in dimethylformamide (50 ml) was added dropwise-to a stirred mixture of 4 -piperidino-2 -picoline (15 g), potassium carbonate (23.5. g) in dimethylformamide (50 ml) at 25°-30°. After 3.5 hours, the mixture was stripped and the residue taken up in water, adjusted to pH 13 with 40 % aqueous NaOH, and extracted with ether. After drying ($K_2CO_3$) and stripping, the residue was chromatographed (silica gel, n-hexane:ether) to give 4 -piperidino-5 -bromo-2 -picoline, 11.18 g, as an oil and 4 -piperidino-3 -bromo-2 -picoline, 3.5 g, as an oil.

EXAMPLE 17 C

Preparation of 4 -piperidino-5 -bromo-2 -picoline-N-oxide m-Chloroperbenzoic acid (7.3 g) in dichloromethane (100 ml) was added dropwise to a stirred solution of 4 -piperidino-5 -bromo-2 -picoline. After 16 hours, the solution was washed with 10 % aqueous sodium carbonate, dried ($K_2CO_3$) and stripped. The residue was chromatographed (silica gel, chloroform:methanol) to give 4 -piperidino-5 -bromo-2 -picoline-N-oxide, 6.79 g, m.p. 115°-6 ° from ether.

EXAMPLE 17D

Preparation of 4-piperidino-5-bromo-2-hydroxymethylpyridine 4-piperidino-5-bromo-2-picoline-N-oxide (4.66 g) and acetic anhydride (25 ml) were heated at 100° for 1.25 hours. The solution was stripped, treated with toluene (30 ml) and stripped again. 2N Hydrochloric acid (35 ml) was added and the mixture heated at 100° for 2 hours. After cooling, 40% aqueous NaOH was added to pH13 and the solution extracted with ether. After drying ($K_2CO_3$) and stripping, the residue was chromatographed (silica gel. chloroform:methanol) to give 4-piperidino-s-bromo-2-hydroxymethylpyridine, 2.38 g, m.p. 118°-9°, from ether.

EXAMPLE 17E

Preparation of 4-piperidino-5-bromo-2-chloromethylpyridine hydrochloride

Substituting 4-piperidino-5-bromo-2-hydroxymethylpyridine (3.0 g) for 4-morpholino-3-chloro-2-hydroxymethylpyridine and using corresponding molar proportions of the other reagents in the method of Example 3E gave 4-piperidino-5-bromo-2-chloromethyl pyridine hydrochloride, 3.47 g, m.p. 155°-7° by ether trituration.

EXAMPLE 17F

Preparation of
2-(4-piperidino-5-bromo-2-pyridylmethylthio)-5-methoxy-(1H)-benzimidazole Substituting 4-piperidino-5-bromo-2-chloromethyl pyridine hydrochloride (3.44 g) for 4-morpholino-3-chloro-2-chloromethylpyridine hydrochloride and using corresponding molar proportions of the other reagents in the method of Example 3F gave after chromatography (silica gel, chloroform:methanol) 2-(4-piperidino-5-bromo-2-pyridylmethylthio)-5-methoxy-(1H)-benzimidazole, 4.39 g, as oil.

EXAMPLE 18

Preparation of
2-(4-piperidino-5-bromo-2-pyridylmethylsulphinyl)-5-methoxy-(1H)-benzimidazole Substituting 2-(4-piperidino-5-bromo-2-pyridylmethylthio)-5-methoxy-(1H)-benzimidazole (3.83 g) for 2-(4-morpholino-3-chloro-2-pyridylmethylthio-5-methoxy-(1H)-benzimidazole and using corresponding molar proportions of the other reagents in the method of Example 4 gave after chromatography (silica gel, chloroform:methanol-ammonia) 2-(4-piperidino-5-bromo-2-pyridylmethylsulphinyl)-5-methoxy-(1H)-benzimidazole, 3.15 g, m.p. 114°–8° C., from ether.

|  | $C_{19}H_{21}BrN_4O_2S$ |
|---|---|
| Found | C 50.48, H 4.78, N 12.30, S 7.13, Br 17.14 |
| Requires | C 50.78, H 4.71, N 12.47, S 7.14, Br 17.78 |

EXAMPLE 19A

Preparation of
4-piperidino-3-bromo-2-picoline-N-oxide

Substituting 4-piperidino-3-bromo-2-picoline (3.46 g) for 4-piperidino-5-bromo-2-picoline and using corresponding molar proportions of the other reagents in the method of Example 17C gave 4-piperidino-3-bromo-2-picoline-N-oxide, 2.5 g. m.p. 98°–100° from pet. ether (60/80).

EXAMPLE 19B

Preparation of
4-piperidino-3-bromo-2-hydroxymethylpyridine

Substituting 4-piperidino-3-bromo-2-picoline-N-oxide (2.42 g) for 4-piperidino-5-bromo-2-picoline-N-oxide and using corresponding molar proportions of the other reagents in the method of Example 17D gave 4-piperidino-3-bromo-2-hydroxymethyl pyridine, 1.19 g, m.p. 51°–3° from pet. ether (40/60).

EXAMPLE 19C

Preparation of
4-piperidino-3-bromo-2-chloromethylpyridine hydrochloride

Substituting 4-piperidino-3-bromo-2-hydroxymethyl-pyridine (0.96 g) for 4-morpholino-3-chloro-2-hydroxymethylpyridine and using corresponding molar proportions of the other reagents in the method of Example 3E gave 4-piperidino-3-bromo-2-chloromethylpyridine hydrochloride, 1.08 g. m.p. 182°–4° C. by ether trituration.

EXAMPLE 19D

Preparation of
2-(4-piperidino-3-bromo-2-pyridylmethylthio)-5-methoxy-(1H)-benzimidazole Substituting 4-piperidino-3-bromo-2-chloromethyl pyridine hydrochloride (1.07 g) for 4-morpholino-3-chloro-2-chloromethylpyridine hydrochloride and using corresponding molar proportions of the other reagents in the method of Example 3F gave 2-(4-piperidino-3-bromo-2-pyridylmethylthio)-5-methoxy-(1H)-benzimidazole, 1.34 g, as an oil.

EXAMPLE 20

Preparation of
2-(4-piperidino-3-bromo-2-pyridylmethylsulphinyl)-5-methoxy-(1H)-benzimidazole Substituting 2-(4-piperidino-3-bromo-2-pyridylmethylthio)-5-methoxy-(1H)-benzimidazole (1.34 g) for 2-(4-morpholino-3-chloro-2-pyridylmethylthio)-5-methoxy-(1H)-benzimidazole and using corresponding molar proportions of the other reagents in the method of Example 4 gave after chromatography (silica gel:2% methanol:chloroform) 2-(4-piperidino-3-bromo-2-pyridylmethyl-sulphinyl)-5-methoxy-(1H)-benzimidazole, 0.62 g. from ether.

|  | $C_{19}H_{21}BrN_4O_2S \cdot H_2O$ |
|---|---|
| Found | C 48.53, H 4.58, N 11.75, S 6.80, Br 17.02 |
| Requires | C 48.82, H 4.96, N 11.99, S 6.86, Br 17.10 |

EXAMPLE 21A

Preparation of 5-bromo-2,3-lutidine-N-oxide m-Chloroperbenzoic acid (71.42 g) in dichloromethane (11) was added dropwise to a stirred solution of 5-bromo-2,3-lutidine (70.0 g) over 1 hour. After 23 hours the solution was cooled to 15° and ammonia gas bubbled through to give a white precipitate, which was filtered off. The filtrate was washed with 5% aqueous sodium sulphite, dried, and stripped to give 5-bromo-2,3-lutidine-N-oxide, 61.78 g, m.p. 80°–2°, from ethyl acetate.

EXAMPLE 21B

Preparation of 5-bromo-4-chloro-2,3-lutidine 5-bromo-2,3-lutidine-N-oxide (30.31 g) was added in portions to phosphorus oxychloride (41.3 ml) at 30°–40°. The mixture was heated to 50°, when an exothermic reaction raised the temperature to reflux. After 30 minutes the solution was cooled and poured onto ice to give a white solid, which was filtered off and discarded. The filtrate was extracted with ether then treated with 40% aqueous sodium hydroxide to pH 7, and extracted again with ether. The latter extract was dried (MgSO$_4$) and stripped to give 5-bromo-4-chloro-2,3-lutidine, 12.0 g as a low melting solid.

EXAMPLE 21C

Preparation of 4-piperidino-5-bromo-2,3-lutidine

Substituting 5-bromo-4-chloro-2,3-lutidine (8.0 g) for 3,4-dichloro-2-hydroxymethyl pyridine and using corresponding molar proportions of the other reagents in the method of Example 3D gave, after chromatography (silica gel, chloroform), 4-piperidino-5-bromo-2,3-lutidine, 7.88 g. as an oil.

EXAMPLE 21D

Preparation of
4-piperidino-5-bromo-2,3-lutidine-N-oxide

Substituting 4-piperidino-5-bromo-2,3-lutidine (8.3 g) for 4-piperidino-5-bromo-2-picoline and using corresponding molar proportions of the other reagents in the method of Example 17C gave 4-piperidino-5-bromo-2,3-lutidine-N-oxide, 5.31 g. m.p. 103°–5°, from ether.

EXAMPLE 21E

Preparation of
4-piperidino-5-bromo-3-methyl-2-hydroxymethylpyridine

Substituting 4-piperidino-5-bromo-2,3-lutidine-N-oxide (4.71 g) for 4-piperidino-5-bromo-2-picoline-N-oxide and using corresponding molar proportions of the other reagents in the method of Example 17D gave 4-piperidino-5-bromo-3-methyl-2-hydroxymethylpyridine, 2.34 g. m.p. 80°–1°, from pet. ether (60/80).

EXAMPLE 21F

Preparation of
4-piperidino-5-bromo-3-methyl-2-chloromethylpyridine hydrochloride Substituting 4-piperidino-5-bromo-3-methyl-2-hydroxymethylpyridine (2.25 g) for 4-morpholino-3-chloro-2-hydroxymethylpyridine and using corresponding molar proportions of the other reagents in the method of Example 3E gave 4-piperidino-5-bromo-3-methyl-2-chloromethylpyridine hydrochloride, 2.68 g. m.p. 177°–9°, by ether trituration.

EXAMPLE 21G

Preparation of
2-(4-piperidino-5-bromo-3-methyl-2-pyridylmethylthio)-5-methoxy-(1H)-benzimidazole Substituting 4-piperidino-5-bromo-3-methyl-2-chloromethylpyridine hydrochloride (2.65 g) for 4-morpholino-3-chloro-2-chloromethylpyridine hydrochloride and using the corresponding molar proportions of the other reagents in the method of Example 3F gave 2-(4-piperidino-5-bromo-3-methyl-2-pyridylmethylthio)-5-methoxy-(1H)-benzimidazole, 2.97 g. m.p. 90°–2° from isopropanol/water.

EXAMPLE 22A

Preparation of
2-(4-piperidino-5-bromo-3-methyl-2-pyridylmethylsulphinyl) -5-methoxy-(1H)-benzimidazole Substituting 2-(4-piperidino-5-bromo-3-methyl-2-pyridylmethylthio)-5-methoxy-(1H)-benzimidazole (2.9 g) for 2-(4-morpholino-3-chloro-2-pyridylmethylthio)-5-methoxy-(1H)-benzimidazole and using corresponding molar proportions of the other reagents in the method of Example 4 gave 2-(4-piperidino-5-bromo-3-methyl-2-pyridylmethylsulphinyl) -5-methoxy-(1H)-benzimidazole, 1.83 g, m.p. 157°–9° (dec), from acetonitrile.

| | $C_{20}H_{23}BrN_4O_2S$ |
|---|---|
| Found | C 51.81, H 5.01, N 11.95, S 6.85, Br 17.18 |

-continued

| | $C_{20}H_{23}BrN_4O_2S$ |
|---|---|
| Requires | C 51.84, H 5.00, N 12.09, S 6.92, Br 17.24 |

EXAMPLE 23A

Preparation of
2-(4-piperidino-3-chloro-5-methyl-2-pyridylmethylthio)-5-(1, 1,2,2-tetrafluoroethoxy)-(1H)-benzimidazole 5N Sodium hydroxide (2 ml) was added to a stirred suspension of 4-piperidino-3-chloro-5-methyl-2-chloromethylpyridine hydrochloride (1.6 g) and 5-(1,1,2,2-tetrafluoroethoxy)-2-mercaptobenzimidazole (1.5 g) in ethanol at room temperature. After standing over night an additional quantity of sodium hydroxide (1 ml) was added and after a further 1 hour the mixture was evaporated at reduced pressure. The residue was chromatographed (silica gel chloroform/methanol 2%) and crystallised from acetonitrile to give 2-(4-piperidino-3-chloro-5-methyl-2-pyridylmethylthio)-5-(1, 1,2,2-tetrafluoroethoxy)-(1H)-benzimidazole, 1.66 g, m.p. 170°–71°.

EXAMPLE 23B

Preparation of
2-(4-piperidino-3-chloro-5-methyl-2-pyridylmethylsulphinyl)-5-(1, 1,2,2-tetrafluoroethoxy)-(1H)-benzimidazole m-Chloroperbenzoic acid (0.75 g total) in dichloromethane (40 ml) was added to a solution of 2-(4-piperidino-3-chloro-5-methyl-2-pyridylmethylthio)-5-(1, 1,2,2-tetrafluoroethoxy)-(1H)-benzimidazole (1.5 g) in dichloromethane (30 ml) at −40° to −50° over a period of 2.5 hours. After a further 0.5 hour ammonia was passed through the solution and the precipitate filtered off and washed well with dichloromethane. The filtrates were evaporated under reduced pressure to give an oil which, on treatment with acetonitrile, gave 2-(4-piperidino-3-chloro-5-methyl-2-pyridylmethylsulphinyl)-5-(1, 1,2,2-tetrafluoroethoxy)-(1H)-benzimidazole, 0.77 g. m.p. 155°–56° (dec).

| | $C_{21}H_{21}ClF_4O_4OS$ |
|---|---|
| Found | C 49.70, H 4.12, N 10.93, S 6.63 |
| Requires | C 49.95, H 4.19, N 11.10, S 6.35 |

EXAMPLE 24A

Preparation of
2-(4-piperidino-3-chloro-5-methyl-2-pyridylmethylthio)-4, 5-difluoromethylenedioxy-(1H)-benzimidazole Substituting 4,5-difluoromethylenedioxy-2-mercaptobenzimidazole (1.5 g) for 5-(1,1,2,2-tetrafluoroethoxy)-2-mercaptobenzimidazole and using corresponding molar proportions of the other reagents in the method of Example 23A gave 2-(4-piperidino-3-chloro-5-methyl-2-pyridylmethylthio)-4, 5-difluoromethylenedioxy-(1H)-benzimidazole, 2.12 g. m.p. 198°–99° from acetonitrile.

EXAMPLE 24B

Preparation of
2-(4-piperidino-3-chloro-5-methyl-2-pyridylmethylsulphinyl)-4,
5-difluoromethylenedioxy-(1H)-benzimidazole Substituting 2-(4-piperidino-3-chloro-5-methyl-2-pyridylmethylthio)-4, 5-difluoromethylenedioxy-(1H)-benzimidazole (2 g) for 2-(4-piperidino-3-chloro-5-methyl-2-pyridylmethylthio)-5-(1, 1,2,2-tetrafluoroethoxy)-(1H)-benzimidazole and using corresponding molar proportions of the other reagents in the method of Example 23B gave 2-(4-piperidino-3-chloro-5-methyl-2-pyridylmethylsulphinyl)-4,5-difluoromethylenedioxy-(1H)-benzimidazole, 1.05 g, m.p. 169°–70° (dec) from acetonitrile.

EXAMPLE 25A

Preparation of 4-chloro-5-bromo-2-picoline-N-oxide

A solution of 5-bromo-4-nitro-2-picoline-N-oxide (30.0 g) in dichloromethane (250 ml) was cooled at 10°, and a solution of phosphoryl chloride (35.5 ml) in dichloromethane (200 ml) added over 15 minutes. The mixture was heated under reflux for 5 hours, allowed to cool to ambient temperature, and allowed to stand for 16 hours. After pouring onto ice (300 ml) and stirring for 15 minutes, the mixture was basified to pH 10 using concentrated aqueous sodium hydroxide. The organic phase was separated off, and the aqueous phase further extracted with chloroform (2×100 ml). The combined organic phases were dried ($K_2CO_3$) and stripped to a solid, which was triturated with petroleum ether (40–60), filtered, washed and dried to yield 4-chloro-5-bromo-2-picoline-N-oxide, 24.08 g, m.p. 121°–4° C.

EXAMPLE 25B

Preparation of
4-chloro-5-bromo-2-hydroxymethylpyridine

A solution of 4-chloro-5-bromo-2-picoline-N-oxide (23.9 g) in dichloromethane (250 ml) was cooled to 10° and trifluoroacetic anhydride (25 ml) added over 20 minutes. The mixture was allowed to warm to ambient temperature, and stand for 7 days. After cooling to 10°, methanol (100 ml) was added, and the solution stripped. The residue was treated with water (150 ml), basified with saturated aqueous sodium carbonate to pH 10, and extracted with ethyl acetate (2×150 ml). The combined extracts were dried ($MgSO_4$), stripped, and triturated with ether to give 4-chloro-5-bromo-2-hydroxymethylpyridine, 16.58 g. m.p. 109°–10°.

EXAMPLE 25C

Preparation of
4-dimethylamino-5-bromo-2-hydroxymethylpyridine

Substituting 33% w/w dimethylamine in ethanol (15 ml) for morpholine and 4-chloro-5-bromo-2-hydroxymethylpyridine (5 g) for 3,4-dichloro-2-hydroxymethylpyridine and using corresponding molar proportions of the other reagents in the method of Example 3D gave after chromatography (silica, chloroform:methanol, 98:2) 4-dimethylamino-5-bromo-2-hydroxymethylpyridine, 3.62 g, as an oil.

EXAMPLE 25D

Preparation of
4-dimethylamino-5-bromo-2-chloromethylpyridine hydrochloride

Substituting 4-dimethylamino-5-bromo-2-hydroxymethylpyridine (3.42 g) for 4-morpholino-3-chloro-2-hydroxymethylpyridine and using corresponding molar proportions of the other reagents in the method of Example 3E gave 4-dimethylamino-5-bromo-2-chloromethylpyridine hydrochloride, 4.11 g, m.p. 184°–5° (dec.).

EXAMPLE 25E

Preparation of
2-(4-dimethylamino-5-bromo-2-pyridylmethylthio)-5-methoxy-(1H)-benzimidazole Substituting 4-dimethylamino-5-bromo-2-chloromethylpyridine hydrochloride (3.96 g) for 4-morpholino-3-chloro-2-chloromethylpyridine hydrochloride and using corresponding molar proportions of the other reagents in the method of Example 3F gave after chromatography 2-(4-dimethylamino-5-bromo-2-pyridylmethylthio)-5-methoxy-(1H)-benzimidazole, 5.23 g, as a foam.

EXAMPLE 25F

Preparation of
2-(4-dimethylamino-5-bromo-2-pyridylmethylsulphinyl)-5-methoxy-(1H)-benzimidazole Substituting 2-(4-dimethylamino-5-bromo-2-pyridylmethylthio)-5-methoxy-(1H)-benzimidazole (5.02 g) for 2-(4-morpholino-3-chloro-2-pyridylmethylthio)-5-methoxy-(1H)-benzimidazole and using corresponding molar proportions of the other reagents in the method of Example 4 gave 2-(4-dimethylamino-5-bromo-2-pyridylmethylsulphinyl)-5-methoxy-(1H)-benzimidazole, 3.8 g.

|  | $C_{16}H_{17}BrN_4O_2S$ |
|---|---|
| Found | C 47.18, H 4.14, N 13.60, S 7.81, Br 19.34 |
| Requires | C 46.95, H 4.19, N 13.69, S 7.83, Br 19.52 |

EXAMPLE 26A

Preparation of
4-pyrrolidino-5-bromo-2-hydroxymethylpyridine

Substituting pyrrolidine (7.4 ml) for morpholine and 4-chloro-5-bromo-2-hydroxymethylpyridine (4 g) for 3,4-dichloro-2-hydroxypyridine and using corresponding molar proportions of the other reagents in the method of Example 3D gave 4-pyrrolidino-5-bromo-2-hydroxymethylpyridine. 2.28 g, m.p. 108°–10° C., from ether.

EXAMPLE 26B

Preparation of
4-pyrrolidino-5-bromo-2-chloromethylpyridine hydrochloride

Substituting 4-pyrrolidino-5-bromo-2-hydroxymethylpyridine (2.17 g) for 4-morpholino-3-chloro-2-hydroxymethylpyridine and using corresponding molar proportions of the other reagents in the method of Example 3E gave 4-pyrrolidino-5-bromo-2-chloromethylpyridine hydrochloride. 2.6 g. m.p. 197°–200° (dec.).

EXAMPLE 26C

Preparation of
2-(4-pyrrolidino-5-bromo-2-pyridylmethylthio)-5-methoxy-(1H)-benzimidazole Substituting 4-pyrrolidino-5-bromo-2-chloromethylpyridine hydrochloride (2.48 g) for 4-morpholino-3-chloro-2-chloromethylpyridine hydrochloride and using corresponding molar proportions of the other reagents in the method of Example 3F gave 2-(4-pyrrolidino-5-bromo-2-pyridylmethylthio)-5-methoxy-(1H)-benzimidazole, 3.37 g, as an oil.

EXAMPLE 26D

Preparation of
2-(4-pyrrolidino-5-bromo-2-pyridylmethylsulphinyl)-5-methoxy-(1H)-benzimidazole Substituting 2-(4-pyrrolidino-5-bromo-2-pyridylmethylthio)-5-methoxy-(1H)-benzimidazole (3.23 g) for 2-(4-morpholino-3-chloro-2-pyridylmethylthio)-5-methoxy-(1H)-benzimidazole and using corresponding proportions of the other reagents in the method of Example 4 gave 2-(4-pyrrolidino-5-bromo-2-pyridylmethylsulphinyl)-5-methoxy-(1H)-benzimidazole, 2.6 g. m.p. (dec. ca. 144°).

EXAMPLE 27

Preparation of
2-(4-morpholino-3-fluoro-2-pyridylmethylthio)-5-Methoxy-(1H)-benzimidazole (i) Sodium nitrite (15.3 g) was added to a stirred solution of 3-amino-2-picoline (20 g) in 40% fluoroboric acid (215 ml) at −5° to −10°. The mixture was stirred for 2 hours at −10° followed by a further 2 hours at room temperature, after which time, the solution was basified (NaOH) and extracted with dichloromethane. The extracts were back-washed with water (pH 6 HCl) to remove some unreacted amine and, after drying (K$_2$CO$_3$), m-chloroperbenzoic acid (35.7 g) was added and the mixture allowed to stand for 16 hours. Ammonia gas was passed through the solution and the precipitated benzoate salts filtered off. The filtrate was evaporated to dryness to give 2-methyl-3-fluoropyridine-N-oxide (13.36 g) m.p. softens 55° melts 80°.

(ii) A nitration mixture of 30% oleum (55 ml) and fuming nitric acid (90 ml) was added dropwise with cooling and stirring to a solution of 2-methyl-3-fluoropyridine-N-oxide (13.3 g) in concentrated sulphuric acid (48 ml) at 10°–15°. The solution was stirred at room temperature for 1.5 hours and then for 2 hours at 100°. After cooling, the mixture was poured onto ice, basified (ammonium carbonate) and extracted with dichloromethane. After drying (K$_2$CO$_3$), the extracts were evaporated to dryness to give 2-methyl-3-fluoro-4-nitropyridine-N-oxide (12.12 g) m.p. 170°–175°.

(iii) Phosphoryl chloride (19 ml) in dichloromethane (50 ml) was added dropwise to a stirred solution of 2-methyl-3-fluoro-4-nitropyridine-N-oxide (12 g) in dichloromethane (50 ml). The reaction mixture was heated under reflux for a total of 8 hours. After cooling and pouring onto ice, the mixture was basified (NaOH) to pH 9 and extracted with dichloromethane. After drying (K$_2$CO$_3$) and removal of solvent, the crude product was purified by column chromatography (silica gel; 1% MeOH/CHCl$_3$) to give 2-methyl-3-fluoro-4-chloro-pyridine-N-oxide (6.78 g) m.p. 63°–65°.

(iv) Trifluoroacetic anhydride (16.18 ml) was added dropwise at 10°–15° to a solution of 2-methyl-3-fluoro-4-chloropyridine-N-oxide (6.17 g) in dichloromethane (50 ml). After three days at room temperature, methanol (30 ml) was added to the cooled solution. The excess solvent was removed and the residue dissolved in water. After basifying (NaOH), the solution was extracted with dichoromethane. The extracts were dried (K$_2$CO$_3$) and evaporated to dryness to give a solid which was purified by column chromatography (silica gel; 1% MeOH/CHCl$_3$) to give 2-hydroxymethyl-3-fluoro-4-chloropyridine (3.8 g) m.p. indeterminate)

(v) A mixture of 2-hydroxymethyl-3-fluoro-4-chloropyridine (2.5 g) and morpholine (6.74 ml) were heated together in a sealed vessel at 180° for 4 hours. The mixture was cooled, washed out with ethanol and stripped. The residue was treated with water (80 ml) and extracted with chloroform. The combined extracts were dried (K$_2$CO$_3$) filtered and excess solvent removed to give a solid which, after chromatography (silica gel 1–2% MeOH/CHCl$_3$). afforded 2-hydroxymethyl-3-fluoro-4-morpholinopyridine (1.75 g) m.p. 138°–142°.

(vi) Thionyl chloride (1.8 ml) in chloroform (15 ml, alumina dried) was added dropwise to a stirred and cooled solution of 2-hydroxymethyl-3-fluoro-4-morpholinopyridine (1.74 g) in chloroform (20 ml). After 2 hours at room temperature the solution was reduced in volume and ether added. The precipitate was filtered off, washed and dried to give 2-chloromethyl-3-fluoro-4-morpholinopyridine hydrochloride (2.1 g) m.p. 203°–205°.

(vii) 5N NaOH (3.39 ml) was added dropwise to a stirred solution of 2-chloromethyl-3-fluoro-4-morpholinopyridine hydrochloride (2.06 g) and 5-methoxy-(1H)-benzimidazole-2-thiol (1.39 g) in ethanol (35 ml). After 3 hours excess solvent was removed and the residue treated with water (80 ml) and extracted with dichloromethane. The extracts were washed with water, dried (K$_2$CO$_3$), excess solvent removed and the residue crystallised from ethyl acetate to yield 2-(4-morpholino-3-fluoro-2-pyridylmethylthio)-5-methoxy-(1H)-benzimidazole (2.16 g) m.p. 121°–123°.

EXAMPLE 28

Preparation of
2-(4-morpholino-3-fluoro-2-pyridylmethylsulphinyl)-5-methoxy-(1H)-benzimidazole m-Chloroperbenzoic acid (1.06 g) in dichloromethane (50 ml) was added dropwise to a stirred solution of 5-methoxy-2-(4-morpholino-3-fluoro-2-pyridylmethylthio)-(1H)-benzimidazole (2.31 g) in dichloromethane (50 ml) at −30° to −35°. After 0.5 hour at −30° a further addition of m-chloroperbenzoic acid (0.106 g) in dichloromethane (15 ml) was made and the mixture stirred for a further 20 minutes at −30°. Ammonia gas was then passed through the solution and the precipitated benzoate salts filtered off. The filtrate was evaporated to dryness and the residue crystallised from ethyl acetate to yield 2-(4-morpholino-3-fluoro-2-pyridylmethylsulphinyl)-5-methoxy-(1H)-benzimidazole (1.75 g) m.p. 142°–46°

| C$_{18}$H$_{19}$FN$_4$O$_3$S | |
|---|---|
| Found | C, 55.46 H, 4.94 N, 14.27 S, 8.08 |

-continued

| | $C_{18}H_{19}FN_4O_3S$ |
|---|---|
| Requires | C, 55.37 H, 4.91 N, 14.35 S, 8.21 |

EXAMPLE 29

Preparation of 2-(4-morpholino-5-fluoro-2-pyridylmethylthio)-5-methoxy-(1H)-benzimidazole (i) Sodium nitrite (43.65 g) was added portionwise to a stirred solution of 5-amino-2-picoline (34.21 g) in water (220 ml) and concentrated hydrochloric acid (158 ml) at −5° to 0° over 30 minutes. After a further 5 minutes at this temperature. 65% hexafluorophosphoric (169 ml) was added dropwise causing precipitation of the hexafluorophosphate salt which was filtered off, washed with water, ethanol and ether and dried under vacuum (76 g). The salt was then added portionwise with rapid stirring to petroleum ether (800 ml, b.p. 120°–160°) at 90°–95° over 30 minutes. After a further 5 minutes the mixture was cooled to room temperature, the petrol decanted and extracted with 2N hydrochloric acid (400 ml). The acidic extract and solid residue were combined, extracted with ether, basified (NaOH) and extracted again with dichloromethane. After drying ($K_2CO_3$), m-chloroperbenzoic acid (65.5 g) was added and the mixture allowed to stand for 16 hours. Ammonia gas was passed through the solution and the precipitated benzoate salts filtered off. Excess solvent was removed from the filtrate to give 2-methyl-5-fluoropyridine-N-oxide (30.24 g) as an oil.

(ii) Substituting 2-methyl-5-fluoropyridine-N-oxide (33.89 g) for 2-methyl-3-fluoropyridine-N-oxide and using corresponding molar proportions of the other reagents in the method of Example 27(ii), gave 2-methyl-4-nitro-5-fluoropyridine-N-oxide (33.09 g) m.p. 100°–105°.

(iii) Substituting 2-methyl-4-nitro-5-fluoropyridine-N-oxide (32.94 g) for 2-methyl-3-fluoro-4-nitropyridine-N-oxide and using corresponding molar proportions of the other reagents in the method of. Example 27(iii), gave 2-methyl-4-chloro-5-fluoropyridine-N-oxide (25.97 g) m.p. 100°–102°.

(iv) Substituting 2-methyl-4-chloro-5-fluoropyridine-N-oxide (13 g) for 2-methyl-3-fluoro-4-chloropyridine-N-oxide and using corresponding molar proportions of the other reagents in the method of Example 27(iv), gave 2-hydroxymethyl-4-chloro-5-fluoropyridine (6.83 g) m.p. 50°–52°.

(v) Substituting 2-hydroxymethyl-4-chloro-5-fluoropyridine (2.5 g) for 2-hydroxymethyl-3-fluoro-4-chloropyridine and using corresponding molar proportions of the other reagents in the method of Example 27(v), gave 2-hydroxymethyl-4-morpholino-5-fluoropyridine (2.08 g) m.p. 134°–136° (from acetonitrile).

(vi) Substituting 2-hydroxymethyl-4-morpholino-5-fluoropyridine (1.98 g) for 2-hydroxymethyl-4-morpholino-3-fluoropyridine and using corresponding molar proportions of the other reagents in the method of Example 27(vi), gave 2-chloromethyl-4-morpholino-5-fluoropyridine hydrochloride (2.45 g) m.p. 224°–226°.

(vii) Substituting 2-chloromethyl-4-morpholino-5-fluoropyridine hydrochloride (2.4 g) for 2-chloromethyl-4-morpholino-3-fluoropyridine and using corresponding molar proportions of the other reagents in the method of Example 27(vii) gave 2-(4-morpholino-5-fluoro-2-pyridylmethylthio)-5-methoxy-(1H)-benzimidazole (2.84 g) m.p. 142°–144° (from ethyl-/acetate/ether).

EXAMPLE 30

Preparation of 2-(4-morpholino-5-fluoro-2-pyridylmethylsulphinyl)-5-methoxy-(1H)-benzimidazole (i) Substituting 2-(4-morpholino-5-fluoro-2-pyridylmethylthio)-5-methoxy-(1H)-benzimidazole (2.77 g) for 2-(4-morpholino-3-fluoro-2-pyridylmethylthio)-5-methoxy-(1H)-benzimidazole and using corresponding molar proportions of the other reagents in the method of Example 28 gave 2-(4-morpholino-5-fluoro-2-pyridylmethylsulphinyl)-5-methoxy-(1H)-benzimidazole (2.08 g) m.p. 109°–111° (from ethyl acetate).

| | $C_{18}H_{19}FN_4O_3.0.15\ H_2O$ |
|---|---|
| Found | C, 55.11 H, 4.91 N, 14.18 S, 7.88 |
| Requires | C, 54.98 H, 4.95 N, 14.25 S, 8.16 |

EXAMPLE 31

Preparation of 2-(4-dimethylamino-3-fluoro-2-pyridylmethylthio)-5-methoxy-(1H)-benzimidazole (i) A mixture of 2-hydroxymethyl-3-fluoro-4-chloropyridine (2.5 g) and 33% dimethylamine in IMS (17 ml) were heated together in a sealed vessel at 180° for 4 hours. The mixture was cooled, washed out with ethanol and stripped. The residue was treated with water (40 ml) and extracted with chloroform. The combined extracts were dried ($K_2CO_3$). filtered and excess solvent evaporated to give a solid which was purified by column chromatography (silica gel; 2% $MeOH/CHCl_3$) to give, after crystallisation ($CHCl_3$ Petroleum ether b.p. 60°–80°), 2-hydroxymethyl-4-dimethylamino-3-fluoropyridine (1.84 g) m.p. 88°–90°.

(ii) Substituting 2-hydroxymethyl-4-dimethylamino-3-fluoropyridine (1.76 g) for 2-hydroxymethyl-3-fluoro-4-morpholinopyridine and using corresponding molar proportions of the other reagents in the method of Example 27(vi), gave 2-chloromethyl-4-dimethylamino-3-fluoropyridine hydrochloride (2.27 g) m.p. 209°–212°.

(iii) Substituting 2-chloromethyl-4-dimethylamino-3-fluoropyridine hydrochloride (2.21 g) for 2-chloromethyl-4-morpholino-3-fluoropyridine hydrochloride and using corresponding molar proportions of the other reagents in the method of Example 27(vii), gave 2-(4-dimethylamino-3-fluoro-2-pyridylmethylthio)-5-methoxy-(1H)-benzimidazole (3.26 g) as an oil.

EXAMPLE 32

Preparation of 2-(4-dimethylamino-3-fluoro-2-pyridylmethylsulphinyl)-5-methoxy-(1H)-benzimidazole Substituting 2-(4-dimethylamino-3-fluoro-2-pyridylmethylthio)-5-methoxy-(1H)-benzimidazole (3.19 g) for 2-(4-morpholino-3-fluoro-2-pyridylmethylthio)-5-methoxy-(1H)-benzimidazole and using corresponding molar proportions of the other reagents in the Example 28, gave 2-(4-dimethylamino-3-fluoro-2-pyridylmethylsulphinyl)-5-methoxy-(1H)-benzimidazole (2.12 g) m.p. 145°–147° (from ethyl acetate).

| C₁₆H₁₇FN₄O₂S 0.044 CH₃COOC₂H₅ | |
| --- | --- |
| Found | C, 55.28 H, 5.03 N, 15.88 S, 9.06 |
| Requires | C, 55.15 H, 4.97 N, 15.90 S, 9.10 |

EXAMPLE 33

Preparation of 2-(4-dimethylamino-5-fluoro-2-pyridylmethylthio)-5-methoxy-(1H)-benzimidazole (i) Substituting 2-hydroxymethyl-4-chloro-5-fluoropyridine (2.5 g) for 2-hydroxymethyl-3-fluoro-4-chloropyridine and using corresponding molar proportions of the other reagents in the method of Example 31(i) gave 2-hydroxymethyl-4-dimethylamino-5-fluoropyridine (2.18 g) m.p. 80°–82°.

(ii) Substituting 2-hydroxymethyl-4-dimethylamino-5-fluoropyridine (2.06 g) for 2-hydroxymethyl-4-morpholino-3-fluoropyridine and using corresponding molar proportions of the other reagents in the method of Example 27(vi), gave 2-chloromethyl-4-dimethylamino-5-fluoropyridine hydrochloride (2.68 g) m.p. 211°–212°.

(iii) Substituting 2-chloromethyl-4-dimethylamino-5-fluoropyridine hydrochloride (2.61 g) for 2-chloromethyl-4-morpholino-3-fluoropyridine hydrochloride and using corresponding molar proportions of the other reagents in the method of Example 27(vii). gave after chromatography (silica gel 1% MeOH/CHCl₃). 2-(4-dimethylamino-5-fluoro-2-pyridylmethylthio)-5-methoxy-(1H)-benzimidazole (3.86 g) as an oil.

EXAMPLE 34

Preparation of 2-(4-dimethylamino-5-fluoro-2-pyridylmethylsulphinyl)-5-methoxy-(1H)-benzimidazole Substituting 2-(4-dimethylamino-5-fluoro-2-pyridylmethylthio)-5-methoxy-(1H)-benzimidazole (3.75 g) for 2-(4-morpholino-3-fluoro-2-pyridylmethylthio)-5-methoxy-(1H)-benzimidazole and using corresponding molar proportions of the other reagents in the method of Example 28, gave 2-(4-dimethylamino-5-fluoro-2-pyridylmethylsulphinyl)-5-methoxy-(1H)-benzimidazole (1.93 g) m.p. 99°–102° (from ethyl acetate).

| C₁₆H₁₇FN₄O₂S | |
| --- | --- |
| Found | C, 55.44 H, 4.90 N, 16.07 S, 9.15 |
| Requires | C, 55.16 H, 4.92 N, 16.08 S, 9.20 |

EXAMPLE 35

Preparation of 2-(4-morpholino-5-fluoro-3-methyl-2-pyridylmethylthio)-5-methoxy-(1H)-benzimidazole (i) Sodium nitrite (5.6 g) was added portionwise to a stirred solution of 5-amino-3-methyl-2-picoline (5 g) in conc. hydrochloric acid (25 ml) and water (30 ml) at −5° to 0° over 15 minutes. After a further 15 minutes at this temperature, 65% hexafluorophosphoric acid (25 ml) was added dropwise causing precipitation of the hexafluorophosphate salt which was filtered off, washed with water, ethanol, and ether and dried under vacuum (12.33 g). The salt was added portionwise, with rapid stirring, to petroleum ether (100 ml, b.p. 120°–160°) at 60° over 20 minutes. After a further 5 minutes the mixture was cooled to room temperature, the petroleum ether layer decanted, and extracted with 2N hydrochloric acid. The acidic and oily residues were combined, extracted with ether, basified (NaOH) and extracted again with dichloromethane. After drying (K₂CO₃), m-chloroperbenzoic acid (8.45 g) was added to the dichloromethane solution and the mixture allowed to stand for 16 hours. Ammonia gas was passed through the solution and the precipitated benzoate salts filtered off. The filtrate was evaporated to dryness to give 2,3-dimethyl-5-fluoropyridine-N-oxide (2.66 g) m.p. indeterminate.

(ii) A nitration mixture of 30% oleum (24 ml) and fuming nitric acid (40 ml) was added dropwise with cooling to a solution of 2,3-dimethyl-5-fluoropyridine-N-oxide (6.64 g) in concentrated sulphuric acid (24 ml) at 10°–15°. The solution was stirred at room temperature for 1.5 hours and then 2 hours at 80°–90°. After cooling, the mixture was poured onto ice, basified (ammonium carbonate) and extracted with dichloromethane. After drying (K₂CO₃), the extracts were evaporated to dryness to give 2,3-dimethyl-4-nitro-5-fluoropyridine-N-oxide (5.88 g) m.p. 80°–83°.

(iii) Phosphoryl chloride (8.6 ml) in dichloromethane (50 ml) was added to a stirred solution of 2,3-dimethyl-4-nitro-5-fluoropyridine (5.8 g) in dichloromethane (100 ml). The reaction mixture was heated under reflux for 4 hours. After cooling and pouring onto ice, the mixture was basified (NaOH) to pH 12 and extracted with dichloromethane. After drying (K₂CO₃) and removal of solvent, the crude product was purified by column chromatography (silica gel, 2%MeOH/CHCl₃) to give 2,3-dimethyl-4-chloro-5-fluoropyridine-N-oxide (4.11 g) m.p. 137°–39°.

(iv) Trifluoroacetic anhydride (9.7 ml) in dichloromethane (20 ml) was added dropwise to a solution of 2,3-dimethyl-4-chloro-5-fluoropyridine-N-oxide (4.0 g) in dichloromethane (35 ml) at 10°–15°. After 16 hours at room temperature, the mixture was poured onto ice and stirred for 15 minutes. After basifying (NaOH) to pH 13, the dichloromethane was separated, dried (K₂CO₃) and evaporated to dryness to yield 2-hydroxymethyl-3-methyl-4-chloro-5-fluoropyridine which was used without further purification.

(v) A mixture of 2-hydroxy-3-methyl-4-chloro-5-fluoropyridine (4 g) and morpholine (9.8 ml) were heated together in a sealed vessel at 180° for 4 hours. The mixture was cooled, washed out with ethanol and evaporated to dryness. The residue was treated with water (80 ml) and extracted with chloroform. The combined extracts were dried (K₂CO₃). filtered and excess solvent removed to give an oil which, after chromatography (silica gel, CHCl₃), afforded 2-hydroxymethyl-3-methyl-4-morpholino-5-fluoropyridine (0.78 g) m.p. indeterminate.

(vi) Thionyl chloride (0.73 ml) in chloroform (5 ml, alumina dried) was added dropwise to a stirred and cooled solution of 2-hydroxy-3-methyl-4-morpholino-5-fluoro pyridine (0.75 g) in chloroform (15 ml). After 2 hours at room temperature the solution was reduced in volume and ether added. The precipitate was filtered off, washed and dried to give 2-chloromethyl-3-methyl-4-morpholino-5-fluoropyridine hydrochloride (0.6 g) m.p.148°–156°.

(vii) 5N NaOH (1.68ml) was added dropwise to a stirred solution of 2-chloromethyl-3-methyl-4-morpholinopyridine hydrochloride (1.2 g) and 5-methoxy-(1H)-benzimidazole-2-thiol (0.77 g) in ethanol (20 ml). After 16 hours and adding a further 0.2 eq 5N NaOH, excess solvent was removed and the residue treated with water (50 ml) and extracted with dichloromethane. The extracts were washed with water, dried ($K_2CO_3$), excess solvent removed and the residue crystallised from ethanol/water to yield 2-(4-morpholino-5-fluoro-3-methyl-2-pyridylmethylthio)-5-methoxy-(1H)-benzimidazole (1.34 g) m.p. 84°–86°.

EXAMPLE 36

Preparation of
2-(4-morpholino-5-fluoro-3-methyl-2-pyridylmethylsulphinyl)-5-methoxy-(1H)-benzimidazole m-Chloroperbenzoic acid (0.48 g) in dichloromethane (10 ml) was added dropwise to a stirred solution of 5-methoxy-2-(4-morpholino-5-fluoro-3-methyl-2-pyridylmethylthio)-(1H)-benzimidazole (1.1 g) in dichloromethane (50 ml) at −30° to −35°. After 0.5 hour at −30° a further addition of m-chloroperbenzoic acid (0.048 g) in dichloromethane (2 ml) was made and the mixture stirred for a further 0.5 hour. After a further addition of m-chloroperbenzoic acid (0.048 g) in dichloromethane (2 ml) and after standing for a further 0.5 hour at −30°, ammonia gas was passed through the solution and the precipitated benzoate salts filtered off. The filtrate was evaporated to dryness and the residue crystallised from ethyl acetate to yield 2-(4-morpholino-5-fluoro-3-methyl -2-pyridylmethylsulphinyl)-5-methoxy-(1H)-benzimidazole (0.8 g) m.p. 158°–160°.

| | $C_{19}H_{21}FN_4O_3S$ |
|---|---|
| Found | C, 56.45 H, 5.16 N, 13.63 S, 7.63 |
| Requires | C, 56.42 H, 5.23 N, 13.85 S, 7.92 |

EXAMPLE 37

Preparation of
2-(4-morpholino-3-fluoro-2-pyridylmethylthio)-5,6-dimethoxy-(1H)-benzimidazole (i) Carbon disulphide (3.8 ml) was added dropwise to a stirred solution of potassium hydroxide (1.8 g) in ethanol (50 ml) causing precipitation of the xanthate salt. 4,5-Dimethoxy-2,3-diaminobenzene (5 g) in ethanol (30 ml) was added dropwise to the stirred xanthate suspension at room temperature and heated under reflux for two hours. After the reflux, acetic acid (2.5 ml) in water (10 ml) was added dropwise and then excess solvent removed from the suspension. The resulting solid was washed with water and dried to give 5,6-dimethoxy-(1H)-benzimidazole-2-thiol (6.05 g) m.p. 278°–280°.

(ii) Substituting 5,6-dimethoxy-(1H)-benzimidazole-2-thiol (1.6 g) for 5-methoxy-(1H)-benzimidazole-2-thiol and using corresponding molar proportions of the other reagents in the method of Example 27(vii), gave 2-(4-morpholino-3-fluoro-2-pyridylmethylthio)-5,6-dimethoxy-(1H)-benzimdazole (1.37 g) m.p. 173°–174°.

EXAMPLE 38

Preparation of
2-(4-morpholino-3-fluoro-2-pyridylmethylsulphinyl)-5,6-dimethoxy-(1H)-benzimidazole Substituting 2-(4-morpholino-3- fluoro-2-pyridylmethylthio)-5,6-dimethoxy-(1H)-benzimidazole (1.2 g) for 2-(4-morpholino-3-fluoro-2-pyridylmethylthio)-5-methoxy-(1H)-benzimidazole and using corresponding molar proportions of the other reagents in the method of Example 28, gave 2-(4-morpholino-3-fluoro-2-pyridylmethylsulphinyl)-5,6-dimethoxy-(1H)-benzimidazole (1.04 g) m.p. 213°–215°.

| | $C_{19}H_{21}FN_4O_4S$ |
|---|---|
| Found | C, 54.17 H, 5.03 N, 13.20 S, 7.28 |
| Requires | C, 54.27 H, 5.03 N, 13.33 S, 7.63 |

EXAMPLE 39

Preparation of
2-(4-morpholino-3-fluoro-2-pyridylmethylthio)-5-methyl-6-methoxy-(1H)-benzimidazole (i) Substituting 4,5-diamino-2-methyl anisole (1.32 g) for 4,5-dimethoxy-2,3-diaminobenzene and using corresponding molar proportions of the other reagents in the method of Example 37, gave 5-methyl-6-methoxy-(1H)-benzimidazole-2-thiol (1.41 g) m.p. >310°.

(ii) Substituting 5-methyl-6-methoxy-(1H)-benzimidazole-2-thiol (1.9 g) for 5,6-dimethoxy-(1H)-benzimidazole-2-thiol and using corresponding molar proportions of the other reagents in the method of Example 37, gave 2-(4-morpholino-3-fluoro-2-pyridylmethylthio)-5-methyl-6-methoxy-(1H)-benzimidazole (1.6 g) m.p. 124°–126°.

EXAMPLE 40

Preparation of
2-(4-morpholino-3-fluoro-2-pyridylmethylsulphinyl)-5-methyl-6-methoxy-(1H)-benzimidazole Substituting 2-(4-morpholino-3-fluoro-2-pyridylmethylthio)-5-methyl-6-methoxy-(1H)-benzimidazole (1.1 g) for 2-(4-morpholino-3-fluoro-2- pyridylmethylthio)-5,6-dimethoxy-(1H)-benzimidazole and using corresponding molar proportions of the other reagents in the method of Example 28, gave 2-(4-morpholino-3-fluoro-2-pyridylmethylsulphinyl)-5-methyl-6-methoxy-(1H)-benzimidazole (0.85 g) m.p. 185°–186°.

| | $C_{19}H_{21}FN_4O_3S$ |
|---|---|
| Found | C, 56.54 H, 5.27 N, 13.69 |
| Requires | C, 56.42 H, 5.23 N, 13.85 |

EXAMPLE 41

Preparation of
2-(4-dimethylamino-3-fluoro-2-pyridylmethylthio)-5, 6-dimethoxy-(1H)-benzimidazole Substituting 5,6-dimethoxy-(1H)-benzimidazole-2-thiol (1.87 g) for 5-methoxy-(1H)-benzimidazole-2-thiol and using corresponding molar proportions of the other reagents in the method of Example 31(iii), gave 2-(4-dimethylamino-3-fluoro-2-pyridylmethylthio)-5,6-dimethoxy-(1H)-benzimidazole (1.53 g) m.p. 142°–144°.

EXAMPLE 42

Preparation of
2-(4-dimethylamino-3-fluoro-2-pyridylmethylsulphinyl)-5, 6-dimethoxy-(1H)-benzimidazole Substituting 2-(4-dimethylamino-3-fluoro-2-pyridylmethylthio)-5, 6-dimethoxy-(1H)-benzimidazole (1.5 g) for 2-(4-dimethylamino-3-fluoro-2-pyridylmethylthio)-

5-methoxy-(1H)-benzimidazole and using corresponding molar proportions of the other reagents in the method of Example 32, gave 2-(4-dimethylamino-3-fluoro-2-pyridylmethylsulphinyl)-5, 6-dimethoxy-(1H)-benzimidazole (0.46 g) m.p. 208°–210°.

| | $C_{17}H_{19}FN_4O_3S$ |
|---|---|
| Found | C 53.69, H 5.14, N 14.67 |
| Requires | C 53.96, H 5.06, N 14.81 |

EXAMPLE 43

Preparation of
2-(4-dimethylamino-5-chloro-2-pyridylmethylthio)-5-methoxy-(1H)-benzimidazole (i) To a solution of 5-chloro-2-methylpyridine-N-oxide (9.46 g) in concentrated sulphuric acid (30 ml), a nitration mixture consisting of 30% oleum (28 ml) and fuming nitric acid (47 ml), was added dropwise at 5°–8° over 20 minutes. The reaction mixture was allowed to stand for one hour at room temperature and then heated for 2 hours on a steam bath After allowing to cool the solution was poured onto ice and carefully neutralised with ammonium carbonate, added in portions. The solid was extracted into chloroform, dried, stripped and triturated with petrol to give 5-chloro-4-nitro-2-methylpyridine-N-oxide, (9.83 g), m.p.120°–122°

(ii) To a stirred and cooled solution of 5-chloro-4-nitro-2-methyl-pyridine-N-oxide (9.7 g) in dichloromethane (100 ml) at 5°–10°, a solution of phosphoryl chloride (14.7 ml) in dichloromethane (100 ml) was added. The solution was heated under reflux for 4.5 hours, poured on ice-water and basified (NaOH) to pH 8–9. The dichloromethane was separated, dried ($K_2CO_3$), stripped and the residue triturated with ether filtered, washed and dried to give 4,5-dichloro-2-methylpyridine-N-oxide, (7.69 g). m.p.120°–123°

(iii) To a stirred and cooled solution of 4,5-dichloro-2-methyl-pyridine-N-oxide (8.54 g) in dichloromethane (110 ml) at 10°–15°, was added trifluoroacetic anhydride (12 ml) and the reaction mixture allowed to stand 6 days. The solution was cooled to 5°–10°, methanol added dropwise and the mixture stripped. The residue was treated with $H_2O$ (70 ml) basified to pH 9–10 ($K_2CO_3$) and extracted with chloroform. The extract was dried ($K_2CO_3$), stripped and the residue triturated with petrol to give 4,5-dichloro-2-hydroxy-methylpyridine, (6.15 g), m.p. 103°–106°

(iv) Substituting 4,5-dichloro-2-hydroxymethylpyridine (3.0 g) for 3,4-dichloro-5-methyl-2-hydroxymethylpyridine and using corresponding molar proportions of the other reagents in the method of Example 15A gave 4-dimethylamino-5-chloro-2-hydroxymethylpyridine, (2.94 g), as an oil.

(v) Substituting 4-dimethylamino-5-chloro-2-hydroxymethylpyridine (2.41 g) for 4-dimethylamino-3-chloro-5-methyl-2-hydroxymethylpyridine and using corresponding molar proportions of the other reagents in the method of Example 15B gave 4-dimethylamino-5-chloro-2-chloromethylpyridine hydrochloride, (2.84 g), m.p. 166°–169°.

(vi) Substituting 4-dimethylamino-5-chloro-2-chloromethylpyridine hydrochloride (2.79 g) for 4-dimethylamino-3-chloro-5-methyl-2-chloromethylpyridine hydrochloride and using corresponding molar proportions of the other reagents in the method of Example 15C gave 2-(4-dimethylamino-5-chloro-2-pyridylmethylthio)-5-methoxy-(1H)-benzimidazole, (3.99 g), as a foam.

EXAMPLE 44

Preparation of 2-(4-dimethylamino-5-chloro-2-pyridyl methylsulphinyl)-5-methoxy-(1H)-benzimidazole Substituting 2-(4-dimethylamino-5-chloro-2-pyridylmethylthio)-5-methoxy-(1H)-benzimidazole (3.88 g) for 2-(4-dimethylamino-3-chloro-5-methyl-2-pyridylmethylthio)-5-methoxy-(1H)-benzimidazole and using corresponding molar proportions of the other reagents, in the method of Example 16, gave 2-(4-dimethylamino-5-chloro-2-pyridylmethylsulphinyl)-5-methoxy-(1H)-benzimidazole, (2.04 g), m.p. 155°–157°

| | $C_{16}H_{17}ClN_4O_2S$ |
|---|---|
| Found | C 52.79, H 4.75, N 15.22, Cl 9.87, S 8.96 |
| Requires | C 52.67, H 4.70, N 15.36, Cl 9.72, S 8.79 |

EXAMPLE 45

Preparation of
2-(4-dimethylamino-5-chloro-2-pyridylmethylthio)-5, 6-dimethoxy-(1H)-benzimidazole Substituting 5,6-dimethoxy-(1H)-benzimidazole-2-thiol (1.57 g) for 5-methoxy-(1H)-benzimidazole and using corresponding molar proportions of the other reagents in the method of Example 42(vi), gave 2-(4-dimethylamino-5-chloro-2-pyridylmethylthio)-5, 6-dimethoxy-(1H)-benzimidazole, (1.47 g), m.p. 116°–117°

EXAMPLE 46

Preparation of
2-(4-dimethylamino-5-chloro-2-pyridylmethylsulphinyl)-5, 6-dimethoxy-(1H)-benzimidazole Substituting 2-(4-dimethylamino-5-chloro-2-pyridylmethylthio)-5, 6-dimethoxy-(1H)-benzimidazole (1.42 g) for 2-(4-dimethylamino-5-chloro-2-pyridylmethylthio)-5-methoxy-(1H)-benzimidazole and using corresponding molar proportions of the other reagents in the method in Example 44, gave 2-(4-dimethylamino-5-chloro-2-pyridylmethylsulphinyl)-5, 6-dimethoxy-(1H)-benzimidazole, (1.37 g), m.p. 164°–165° with decomp.

| | $C_{17}H_{19}ClN_4O_3S$ 0.17 $CH_2Cl_2$ |
|---|---|
| Found | C 50.66, H 4.83, N 13.63, Cl 11.88, S 8.12 |
| Requires | C 50.38, H 4.76, N 13.69, Cl 11.61, S 7.83 |

EXAMPLE 47

Preparation of
2-(4-dimethylamino-3-chloro-2-pyridylmethylthio)-5-methoxy-(1H)-benzimidazole (i) Substituting 3,4-dichloro-2-hydroxymethyl pyridine (5.0 g) for 3,4-dichloro-5-methyl-2-hydroxymethylpyridine and using corresponding molar proportions of the other reagents in the method of Example 15A gave 4-dimethylamino-3-chloro-2-hydroxymethylpyridine, (4.9 g), as an oil.

(ii) Substituting 4-dimethylamino-3-chloro-2-hydroxymethylpyridine (4.3 g) for 4-dimethylamino-3-chloro-5-methyl-2-hydroxymethylpyridine and using corresponding molar proportions of the other reagents in the method of Example 15B gave 4-dimethylamino-3- chloro-2-chloromethylpyridine hydrochloride, (5.52 g), m.p. 194°–196°.

(iii) Substituting 4-dimethylamino-3-chloro-2-chloromethylpyridine hydrochloride (5.0 g) for 4-dimethylamino-3-chloro-5-methyl-2-chloromethylpyridine hydrochloride and using corresponding molar proportions of the other reagents in the method of Example 15C gave 2-(4-dimethylamino-3-chloro-2-pyridylmethylthio)-5-methoxy-(1H)-benzimidazole, (7.11 g), as a foam.

EXAMPLE 48

Preparation of 2-(4-dimethylamino-3-chloro-2-pyridylmethylsulphinyl)-5-methoxy-(1H)-benzimidazole Substituting 2-(4-dimethylamino-3-chloro-2-pyridylmethylthio)-5-methoxy-(1H)-benzimidazole (3.43 g) for 2-(4-dimethylamino-3-chloro-5-methyl-2-pyridylmethylthio)-5-methoxy-(1H)-benzimidazole and using corresponding molar proportions of the other reagents in the method of Example 16, gave 2-(4-dimethylamino-3-chloro-2-pyridylmethylsulphinyl)-5-methoxy-(1H)-benzimidazole, (0.83 g), m.p. 113°–114° from ethyl acetate.

| $C_{16}H_{17}ClN_4O_2S$ | |
| --- | --- |
| Found | C 53.03, H 4.70, N 15.26, Cl 9.77, S 8.65 |
| Requires | C 52.67, H 4.70, N 15.36, Cl 9.72, S 8.79 |

EXAMPLE 49

Preparation of 2-(4-dimethylamino-3-chloro-2-pyridylmethylthio)-5,6-dimethoxy-(1H)-benzimidazole Substituting 5,6-dimethoxy-(1H)-benzimidazole-2-thiol (2.1 g) for 5-methoxy-(1H)-benzimidazole-2-thiol and using corresponding molar proportions of the other reagents in the method of Example 46(iii), gave 2-(4-dimethylamino-3-chloro-2-pyridylmethylthio)-5,6-dimethoxy-(1H)-benzimidazole (2.79 g), m.p. 121°–122°.

EXAMPLE 50

Preparation of 2-(4-dimethylamino-3-chloro-2-pyridylmethylsulphinyl)-5, 6-dimethoxy-(1H)-benzimidazole Substituting 2-(4-dimethylamino-3-chloro-2-pyridylmethylthio)-5,6-dimethoxy-(1H)-benzimidazole (2.72 g) for 2-(4-dimethylamino-3-chloro-2-pyridylmethylthio)-5-methoxy-(1H)-benzimidazole and using corresponding molar proportions of the reagents in the method of Example 48, gave 2-(4-dimethylamino-3-chloro-2-pyridylmethylsulphinyl)-5,6- dimethoxy-(1H)-benzimidazole, (2.11 g), m.p. indeterminate from chloroform/ethyl acetate.

| $C_{17}H_{19}ClN_4O_3S$ 0.9% $CH_3COOC_2H_5$ 0.5% $CHCl_3$ | |
| --- | --- |
| Found | C 51.77, H 4.94, N 13.91, Cl 9.56 |
| Requires | C 51.52, H 4.87, N 13.99, Cl 9.29 |

EXAMPLE 51

Preparation of 2-(4-dimethylamino-3-chloro-5-methyl-2-pyridylmethylthio)-5, 6-dimethoxy-(1H)-benzimidazole Substituting 5,6-dimethoxy-(1H)-benzimidazole-2-thiol (1.65 g) for 5-methoxy-(1H)-benzimidazole-2-thiol and using corresponding molar proportions of the other reagents in the method of Example 15C gave 2-(4-dimethylamino-3-chloro-5-methyl-2-pyridylmethylthio)-5,6-dimethoxy-(1H)-benzimidazole, (1.77 g), m.p. 120°–122°

EXAMPLE 52

Preparation of 2-(4-dimethylamino-3-chloro-5-methyl-2-pyridylmethylsulphinyl)-5, 6-dimethoxy-(1H)-benzimidazole Substituting 2-(4-dimethylamino-3-chloro-5-methyl-2-pyridyl-methylthio)-5, 6-dimethoxy-(1H)-benzimidazole (1.5 g) for 2-(4-dimethylamino-3-chloro-5-methyl-2-pyridylmethylthio)-5-methoxy-(1H)-benzimidazole and using corresponding molar proportions of the other reagents in the method of Example 16, gave 2-(4-dimethylamino-3-chloro-5-methyl-2-pyridylmethylsulphinyl)-5, 6-dimethoxy-(1H)-benzimidazole, (0.87 g), m.p. 174°–175° from dichloromethane.

| $C_{18}H_{21}ClN_4O_3S$ $0.078CH_2Cl_2$ | |
| --- | --- |
| Found | C 52.13, H 5.03, N 13.11 |
| Requires | C 52.25, H 5.13, N 13.48 |

EXAMPLE 53

Preparation of 2-(4-morpholino-3-chloro-2-pyridylmethylthio)-5, 6-dimethoxy-(1H)-benzimidazole Substituting 5,6-dimethoxy-(1H)-benzimidazole-2-thiol (2.22 g) for 5-methoxy-(1H)-benzimidazole-2-thiol and using corresponding molar proportions of the other reagents in the method of the Example 3F, gave 2-(4-morpholino-3-chloro-2-pyridylmethylthio)-5,6-dimethoxy-(1H)-benzimidazole (3.62 g), m.p. 109°–112°.

EXAMPLE 54

Preparation of 2-(4-morpholino-3-chloro-2-pyridylmethylsulphinyl)-5, 6-dimethoxy-(1H)-benzimidazole Substituting 2-(4-morpholino-3-chloro-2-pyridylmethylthio)-5,6-dimethoxy-(1H)-benzimidazole (3.52 g) for 2-(4-morpholino-3-chloro-2-pyridylmethylthio)-5-methoxy-(1H)-benzimidazole and using corresponding molar proportions of the other reagents in the method of Example 4, gave 2-(4-morpholino-3-chloro-2-pyridylmethylsulphinyl)-5, 6-dimethoxy-(1H)-benzimidazole, (2.88 g), m.p. indeterminate from chloroform/ethyl acetate.

| $C_{19}H_{21}ClN_4O_4S$ | |
| --- | --- |
| Found | C 52.35, H 4.94, N 12.71, Cl 8.41, S 7.09 |
| Requires | C 52.23, H 4.84, N 12.82, Cl 8,11, S 7.34 |

EXAMPLE A

A tablet for oral administration is prepared by combining

| | Mg/Tablet |
|---|---|
| Compound of structure (I) | 100 |
| Mannitol | 153 |
| Starch | 33 |
| crospovidone | 12 |
| microcrystalline cellulose | 30 |
| magnesium stearate | 2 |
| | 330 mg | into a 9 mm tablet. If the active ingredient is a compound of structure (I) in which n is 1 then the tablet is provided with an enteric coating.

EXAMPLE B

A pellet formulation for oral administration may be prepared by formulating the following into pellets by standard techniques

| | % w:w |
|---|---|
| Compound of structure (I) | 80 |
| microcrystalline cellulose | 10 |
| sodium carboxymethylcellulose | 2 |
| lactose | 8 |

If the active ingredient is a compound of structure (I) in which n is 1, the pellets are first enteric coated before being filled into hard gelatin capsules.

EXAMPLE C

An injection for parenteral administration is prepared by combining

| | % w:w |
|---|---|
| Compound of example 1 | 1–5 |
| polypropylene glycol | 40 |
| ethanol | 10 |
| water for injection EP to | 100 |

The solution is then sterilised and sealed into 2 ml and 5 ml ampoules and vials.

EXAMPLE D

A reconstitutable lyophilisate for parenteral administration is prepared from:

| | % w:w |
|---|---|
| Compound of structure (I) as a salt | 1–5 |
| Mannitrol | 15 |
| NaCl | sufficient to make reconstituted solution isotonic |
| water to | 100 |

The solution is sterilised by aseptic filtration, 5 ml portions dispensed into 15 ml vials and the solution lyophilised. The lyophilisate can be reconstituted with 10 ml $H_2O$.

BIOLOGICAL DATA

A. $K^+$ Stimulated ATPase Activity

The effects of a single high concentration (1 mM) of a compound of structure (I) on $H^+$-$K^+$ ATPase were determined at pH 6.1 and pH 7.4. Preferred compounds of structure (I) were also tested over a range of concentrations to determine $IC_{50}$ values at pH 6.1 and 7.4.

(i) Preparation of Lyophilised Gastric Vesicles ($H^+$-$K^+$-ATPase)

$H^+$-$K^+$-ATPase was prepared from the lyophilised gastric vesicles of pig fundic mucosa after the method of Saccomani et. al. (Biochem and Biophys. Acta., 465, 311, 1977).

(ii) $K^+$ Stimulated ATPase Activity

Compounds of structure (I) were pre-incubated with $H^+$-$K^+$-ATPase preparation 30 μg protein/ml from (i) in 10 mM Pipes/Tris buffer pH 6.1 and pH 7.4.

After 30 min at 37° the preincubation was diluted 5-fold with assay buffer to start the ATPase reaction. The conditions in the assay are 100 mM Pipes/Tris, 2 mM $MgCl_2$, 10 mM KCl, 5 μgml nigericin, 2 mM $Na_2ATP$, pH 7.0. After an incubation at 37, for 15 min the inorganic phosphate released was determined by the method of Yoda & Hokin (Biochem. Biophys. Res. Com. 40, 880, 1970). Nigericin was dissolved in methanol, which at the final concentration of 0.5%, did not affect the enzyme activity.

The effect of the same concentration of compound of structure (I) (preincubated with $H^+$-$K^+$-ATPase preparation at pH 7.4 as described above) on the recovery of 100 nmole of inorganic phosphate was also determined.

Compounds of structure (I) were initially dissolved in dimethyl sulphoxide, polyethylene glycol (Type 400) or Pipes/Tris buffer. None of these solvents affects $K^+$-ATPase activity at the concentrations used.

All data refer to the concentration of compound present in the preincubation before dilution with assay buffer.

(iii) Results

The compounds of Examples 2, 4, 6, 8. 10, 12, 14, 16, 18, 20, 22, 23, 24, 25 and 26 were all found to inhibit potassium stimulated ATPase activity in the above preparations at pH 6.1 and 7.4.

B. Aminopyrine (AP) accumulation in intact gastric glands

The effect of a single concentration (100 μm) of a compound of structure (I) on dibutyryl cAMP stimulated AP metabolism in rabbit intact gastric glands was determined. Preferred compounds of structure (I) were tested over a range of concentrations to determine the $IC_{50}$ value.

(i) Preparation of intact gastric glands

Intact gastric glands were prepared from New Zealand white rabbits by the method of Berghindh et al. (Acta. Physio. Scand. 96, 150, 1976). Gastric mucosal scrapings were digested at 37° C. for 45–60 min. with Collagenase (100 U. Type 1. Sigma), and glands harvested by coarse filtration and sedimentation.

(ii) AP accumulation

Test compound was incubated with glands and 300 μM dibutyryl CAMP for 30 minutes at 370° C. Incubating medium contained 132.5 mM NaCl, 5.4 Mm KCl, 1.0 mM $NaH_2PO_4$. 5.0 mM $Na_2HPO_4$, 1.2 mM $MgSO_4$, 1.0 mM $CaCl_2$, 11.1 mM glucose, 2.0 mg/ml rabbit albumin, 10 μg/ml phenol red, approximately 0.3 μM[$^{14}$C] aminopyrine (110 mCi/mmole), pH 7.4.

After incubation, glands were centrifuged and the supernatant removed. The glands were dried, weighed and dissolved in NaOH. The distribution of radioactivity between the supernatant and glands is then used to calculate the AP ratio after the method of Berglindh et al. (Acta. Physiol. Scand. 97, 401, 1976).

The $IC_{50}$ value is the amount of compound required to inhibit the histamine stimulated accumulation of aminopyrine by 50%.

(iii) Results

| Compound of Example | $IC_{50}$ (μM) |
|---|---|
| 2 | 6.6 |
| 4 | 11.0 |
| 6 | 16.3 |
| 8 | 4.2 |
| 10 | 2.0 |
| 12 | 1–10.00 |
| 14 | 2.6 |
| 16 | 3.7 |
| 18 | 1.6 |
| 20 | 1.3 |
| 22 | 9.2 |
| 23 | 1.9 |

C. Rat: Lumen Perfumed Stomach (Histamine Stimulated Gastric Acid Secretion)

Using a modification of the procedure described by Ghosh and Schild (Br. J. Pharmacology, 13, 54, 1958), $ED_{50}$ values after either intraduodenal (i.d) or intravenous (i.v) administration were obtained as follows:

| Compound of Example | Route of Administration | $ED_{50}$ μmol/kg or % inhibition at 1 μM/kg |
|---|---|---|
| 2 | i.v. | 1.46 |
| 4 | i.v. | 1.17 |
| 6 | i.d. | 1.94 |
| 8 | i.d. | 2.38 |
| 14 | i.v. | 0.82 |
| 16 | i.d. | 1.46 |
| 18 | i.v. | 0.85 |
| 20 | i.v. | 0.86 |
| 22 | i.d. | 4.55 |
| 28 | i.v. | 0.7 |
| 30 | i.v. | 51% |
| 32 | i.v. | 26% |
| 34 | i.v. | 37% |
| 38 | i.v. | 33% |
| 40 | i.v. | 1.51 |
| 42 | i.v. | 46% |

B. Dog: Conscious Heidenhain Pouch (Histamine-Stimulated Gastric Acid Secretion)

Using dogs surgically prepared with Heidenhain pouches 1 to 3 years previously, inhibitory $ED_{50}$ values against histamine stimulated gastric acid secretion after intravenous administration were obtained.

| Example | $ED_{50}$ μm/kg |
|---|---|
| 2 | 2.94 |
| 4 | 1.00 |
| 6 | 2.20 |
| 10 | 1.20 |
| 16 | 0.29 |
| 25 | 0.91 |
| 28 | 2.75 |
| 30 | 5.07 |
| 36 | 2.05 |
| 40 | 2.14 |

No overt signs of toxicity were observed in any of the foregoing tests.

What is claimed is:

1. A compound of structure (I)

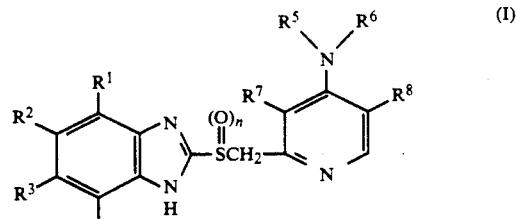

in which, $R^1$ to $R^4$ are the same or different and are each hydrogen, halogen, trifluoromethyl, $C_{1-6}$ alkyl, $C_{1-6}$ alkoxy, $C_{1-6}$ alkanoyl or $C_{1-6}$ alkoxycarbonyl, $RCF_2O$, an ethoxy group substituted by 3 to 5 fluorine atoms;

R is hydrogen or fluorine;

m is 1 or 2;

n is 0 or 1;

$R_5$ and $R^6$ are the same or different and are each $C_{1-6}$ alkyl or $R^5$ and $R^6$ together with the nitrogen atom to which they are attached form a piperidino or morpholino- group; and one of $R^7$ and $R^8$ is halogen, and the other is hydrogen or $C_{1-6}$ alkyl;

or a pharmaceutically acceptable salt thereof, provided that when $R^5$ and $R^6$ are both alkyl, one of $R^7$ and $R^8$ is halogen and the other is $C_{1-6}$ alkyl.

2. A compound as claimed in claim 1 in which n is 1.

3. A compound as claimed in claim 2 in which $R^5$ and $R^6$ together with the nitrogen atom to which they are attached form a piperidino, or morpholino group.

4. A compound as claimed in claim 1 which is: 2-(5-bromo-4-piperidino-2-pyridylmethylsulphinyl)-5-methoxy-(1H)-benzimidazole.

5. A compound as claimed in claim 1 which is: 2-(3-bromo-4-piperidino-2-pyridylmethylsulphinyl)-5-methoxy-(1H)-benzimidazole.

6. A compound as claimed in claim 1 which is: 2-(3-chloro-4-piperidino-2-pyridylmethylsulphinyl)-5-methoxy-(1H)-benzimidazole.

7. A compound as claimed in claim 1 which is: 2-(3-methyl-5-bromo-4-piperidino-2-pyridylmethylsulphinyl)-5-methoxy-(1H)-benzimidazole.

8. A compound as claimed in claim 1 which is: 2-(3-chloro-5-methyl-4-piperidino-2-pyridylmethylsulphinyl)-5-methoxy-(1H)-benzimidazole.

9. A compound as claimed in claim 1 which is: 2-(3-chloro-4-morpholino-2-pyridylmethylsulphinyl)-5-methoxy-(1H)-benzimidazole.

10. A compound as claimed in claim 1 which is: 2-(3-chloro-5-methyl-4-morpholino-2-pyridylmethylsulphinyl)-5-methoxy-(1H)-benzimidazole.

11. A compound as claimed in claim 1 which is: 2-(3-chloro-5-methyl-4-piperidino-2-pyridylmethylsulphinyl)-5-(1, 1,2,3-tetrafluoroethoxy)-(1H)-benzimidazole.

12. A compound as claimed in claim 1 which is: 2-(4-morpholino-3-fluoro-2-pyridylmethylsulphinyl)-5-methoxy-(1H)-benzimidazole.

13. A compound as claimed in claim 1 which is: 2-(4-morpholino-3-fluoro-2-pyridylmethylsulphinyl)-4,5-dimethoxy-(1H)-benzimidazole.

14. A compound as claimed in claim 1 which is: 2-(4-morpholino-5-fluoro-2-pyridylmethylsulphinyl)-5-methoxy-(1H)-benzimidazole.

15. A compound as claimed in claim 1 which is: 2-(4-morpholino-3-methyl-5-fluoro-2-pyridylmethylsulphinyl)-5-methoxy-(1H)-benzimidazole.

16. A compound as claimed in claim 1 which is: 2-(4-morpholino-3-fluoro-2-pyridylmethylsulphinyl)-5-methyl-6-methoxy-(1H)-benzimidazole.

17. A compound as claimed in claim 1 which is 2-(4-dimethylamino-3-chloro-5-methyl-2-pyridylmethylsulphinyl)-5-methoxy-1(H)-benzimidazole.

18. A pharmaceutical composition comprising a compound as claimed in claim 1 in association with a pharmaceutically acceptable carrier.

19. A pharmaceutical composition comprising a compound as claimed in claim 2, in association with a pharmaceutically acceptable carrier.

20. A pharmaceutical composition as claimed in claim 18, in a form suitable for oral administration.

21. A pharmaceutical composition as claimed in claim 19, provided with an enteric coating.

22. A pharmaceutical composition according to claim 18 in which the compound of structure (I) is 2-(3-chloro-4-morpholino-2-pyridylmethylsulphinyl)-5-methoxy-(1H)-benzimidazole.

23. A pharmaceutical composition according to claim 18 in which the compound of structure (I) is 2-(4-dimethylamino-3-chloro-5-methyl-2-pyridylmethylsulphinyl)-5-methoxy-1(H)-benzimidazole.

24. A method of inhibiting gastric acid secretion which comprises administering to a mammal in need thereof an effective amount of a compound as claimed in claim 1.

25. A method of treatment of gastro-intestinal diseases and other conditions caused or exacerbated by gastric acidity which comprises administering to a mammal in need thereof an effective amount of a compound as claimed in claim 1.

* * * * *